(12) United States Patent
Gråskov et al.

(10) Patent No.: US 8,506,524 B2
(45) Date of Patent: Aug. 13, 2013

(54) USER INTERFACE FOR DELIVERY SYSTEM COMPRISING DIARY FUNCTION

(75) Inventors: Henning Gråskov, Bagsværd (DK); Jørgen Smedegaard, Vanløse (DK); Johnny Kristensen, Roskilde (DK); Marianne Lindgård Witt, Hillerød (DK); Anders Geert-Jensen, Risskov (DK)

(73) Assignee: Novo Nordisk A/S, Bagsvaerd (DK)

( * ) Notice: Subject to any disclaimer, the term of this patent is extended or adjusted under 35 U.S.C. 154(b) by 419 days.

(21) Appl. No.: 12/443,868

(22) PCT Filed: Oct. 3, 2007

(86) PCT No.: PCT/EP2007/060511
§ 371 (c)(1),
(2), (4) Date: Aug. 5, 2009

(87) PCT Pub. No.: WO2008/040765
PCT Pub. Date: Apr. 10, 2008

(65) Prior Publication Data
US 2009/0326445 A1    Dec. 31, 2009

(30) Foreign Application Priority Data
Oct. 4, 2006 (EP) .................................. 06121721

(51) Int. Cl.
*A61M 37/00* (2006.01)
*G06F 3/048* (2006.01)

(52) U.S. Cl.
USPC ............. 604/67; 604/131; 715/764; 715/810; 345/156

(58) Field of Classification Search
USPC .......................................... 604/131; 345/156
See application file for complete search history.

(56) References Cited

U.S. PATENT DOCUMENTS

| 4,553,958 | A   | 11/1985 | LeCocq             |
|-----------|-----|---------|--------------------|
| 6,198,383 | B1* | 3/2001  | Sekura et al. ............. 340/309.4 |
| 6,423,035 | B1  | 7/2002  | Das et al.         |
| 6,427,088 | B1  | 7/2002  | Bowman et al.      |
| 6,551,276 | B1  | 4/2003  | Mann et al.        |

(Continued)

FOREIGN PATENT DOCUMENTS

| CN | 1335549  | 2/2002 |
|----|----------|--------|
| DE | 19840965 | 9/1998 |

(Continued)

OTHER PUBLICATIONS

English Abstract of DE19840965 Published Sep. 8, 1998.

(Continued)

*Primary Examiner* — Shyue Jiunn Hwa
(74) *Attorney, Agent, or Firm* — Wesley A. Nicolas; Marc A. Began; Reza Green

(57) ABSTRACT

A device for displaying information is provided. The device includes data storage circuitry for storing data, a display configured to display data to a user, a processor configured to control the display and the data storage circuitry, and user input circuitry. The processor is configured to control the display based on user input to: graphically display an aggregate period view having at least two period views, graphically display a single period view, graphically display a data type symbol corresponding to a given data type, graphically display at least one data type symbol for every period view, and display a card view including information data corresponding to a selected data type symbol.

10 Claims, 26 Drawing Sheets

(56) References Cited

U.S. PATENT DOCUMENTS

| | | |
|---|---|---|
| 6,659,948 B2 | 12/2003 | Lebel et al. |
| 6,740,059 B2 | 5/2004 | Flaherty |
| 6,752,787 B1 | 6/2004 | Causey et al. |
| 6,852,104 B2 | 2/2005 | Blomquist |
| 6,875,195 B2 | 4/2005 | Choi |
| 7,133,329 B2 | 11/2006 | Skyggebjerg et al. |
| 2001/0041869 A1 | 11/2001 | Causey et al. |
| 2002/0065454 A1 | 5/2002 | Lebel et al. |
| 2003/0055323 A1 | 3/2003 | Choi et al. |
| 2003/0060765 A1 | 3/2003 | Campbell et al. |
| 2003/0065308 A1 | 4/2003 | Lebel et al. |
| 2003/0114836 A1 | 6/2003 | Estes et al. |
| 2003/0160683 A1 | 8/2003 | Blomquist |
| 2003/0163223 A1 | 8/2003 | Blomquist |
| 2003/0163789 A1 | 8/2003 | Blomquist |
| 2003/0212379 A1 | 11/2003 | Bylund et al. |
| 2004/0225252 A1 | 11/2004 | Gillespie, Jr. et al. |
| 2005/0022274 A1 | 1/2005 | Campbell et al. |
| 2005/0030164 A1 | 2/2005 | Blomquist |
| 2005/0043863 A1 | 2/2005 | Ali et al. |
| 2005/0182366 A1 | 8/2005 | Vogt et al. |
| 2005/0192561 A1 | 9/2005 | Mernoe |
| 2006/0161865 A1* | 7/2006 | Scott et al. .................... 715/810 |
| 2007/0142822 A1 | 6/2007 | Remde |
| 2007/0194890 A1* | 8/2007 | Brue ........................ 340/309.16 |
| 2008/0147050 A1* | 6/2008 | Mann et al. ................. 604/890.1 |
| 2008/0171967 A1* | 7/2008 | Blomquist et al. .............. 604/67 |

FOREIGN PATENT DOCUMENTS

| | | |
|---|---|---|
| EP | 424687 | 5/1991 |
| EP | 1177802 | 6/2002 |
| EP | 1494158 | 1/2005 |
| EP | 1801718 | 12/2005 |
| WO | WO0029047 | 11/1999 |
| WO | WO02/066101 | 8/2002 |
| WO | WO2006/089958 | 8/2003 |
| WO | WO2004/093648 | 11/2004 |
| WO | WO2005/018716 | 3/2005 |
| WO | WO2005/094919 | 10/2005 |
| WO | WO/2007000425 | 1/2007 |

OTHER PUBLICATIONS

English Abstract of CN1335549 Published Feb. 13, 2002.
Office Action Mailed May 1, 2009 for U.S. Appl. No. 11/917,172, filed Dec. 11, 2007 by Rasmus Panduro.
Final Action Mailed Nov. 7, 2009 for U.S. Appl. No. 11/917,172, filed Dec. 11, 2007 by Rasmus Panduro.
Office Action Mailed Aug. 10, 2009 for U.S. Appl. No. 11/917,073, filed Dec. 10, 2007 by Rasmus Panduro.
Final Action Mailed Apr. 6, 2010 for U.S. Appl. No. 11/917,073, filed Dec. 10, 2007 by Rasmus Panduro.

* cited by examiner

USER INTERFACE FOR DELIVERY SYSTEM COMPRISING DIARY FUNCTION

CROSS-REFERENCE TO RELATED APPLICATIONS

This application is a 35 U.S.C. §371 national stage application of International Patent Application PCT/EP2007/060511 (published as WO 2008/040765), filed Oct. 3, 2007, which claimed priority of European Patent Application 06121721.2, filed Oct. 4, 2006; this application further claims priority under 35 U.S.C. §119 of U.S. Provisional Application 60/849,916, filed Oct. 6, 2006.

The present invention generally relates to electronically controlled drug delivery systems and devices. In a specific embodiment the invention relates to a medical delivery device in combination with a user operated interface for navigating a diary function of the delivery device, however, the different aspects of the present invention is applicable for all types of devices or systems for which a user has to store and display data.

BACKGROUND OF THE INVENTION

In the disclosure of the present invention reference is mostly made to the treatment of diabetes by infusion of insulin, however, this is only an exemplary use of the present invention.

Drug delivery devices for delivering a drug such as insulin to a patient are well known and generally comprise a reservoir adapted to contain a liquid drug, a pump assembly for expelling a drug out of the reservoir to the patient. Such devices are often termed infusion pumps and are normally provided with a user interface allowing a user to control the operation of the pump. The user interface provided on some of the first pumps allowed the user to change a basal infusion rate and program a bolus infusion of a desired size. More recent infusion pumps have provided a number of more advanced features such as a number of basal rates to choose among, temporal basal, bolus calculations based on blood glucose (BG) input and/or meal size, diary functions, food data bases, connectivity to external devices, e.g. BG meter (BGM), PC, PDA or mobile phone.

An infusion pump may basically be a remotely controlled implantable pump or an external pump carried outside the human body and connected thereto by a transcutaneous access device such as a soft cannula or a needle. The external pump may be a traditional durable pump adapted to e.g. be worn in a belt at the waist of the user, this allowing the user to operate the pump by directly accessing the user interface on the pump, e.g. in order to change infusion rate or to program a bolus infusion. However, the pump may also be worn hidden under clothing this making operation more difficult. Correspondingly, it has been proposed to provide an infusion pump of the durable type with a wireless remote controller allowing the user to access some or all of the functionality of the pump, see for example U.S. Pat. No. 6,551,276, US 2005/0022274 and US 2003/0065308, which are hereby incorporated by reference, the latter disclosing an ambulatory medical device (MD) adapted to receive control messages from a communication device (CD).

As traditional durable external pumps are relatively expensive it has been proposed to provide disposable pumps which may be attached directly to the skin of the user by means of an adhesive at a lower surface of such a device. A disposable pump may be provided to the user prefilled or it may be adapted to be filled by the user. Correspondingly, the pump may be a unitary fully disposable device or it may comprise two or more portions adapted to be used for different periods of time. Thus, for a skin-mountable device, typically comprising an adhesive allowing the device to be attached directly to the skin of the user, a remote controller would appear even more desirable as it would reduce the cost of providing a full user interface on the pump. Correspondingly, EP 1 177 802 and U.S. Pat. No. 6,740,059, which are hereby incorporated by reference, disclose semi-disposable and fully disposable infusion devices (which may be termed a local device or unit) which are intended to be operated primarily or entirely by a wireless remote controller (which may be termed a remote device or unit). As the delivery device thus does not have to be provided with a user interface such as a display and keyboard, the semi-disposable or disposable infusion can be provided more cost-effectively.

A drug delivery system, either as a unitary device or as a system comprising e.g. a drug delivery pump and a remote controller, or adapted to communicate with external units, e.g. a PDA or PC, may be provided with a diary function allowing data to be stored, either automatically or by the user. For example, a drug delivery system may be store infusion data such as bolus and temporal basal, blood glucose data such BG values and other data such as meal size and medicine taken. EP 1 494 158 discloses a system and method for managing presentation of medical data, involving presenting medical data, e.g. BG values, downloaded from a device in selected graphical display charts in visual display. US 2005/0022274 discloses a drug delivery system comprising a remote controller with a memory and display allowing the user to store and retrieve data, e.g. BG values which can be displayed either as values or as a graph for one or more days.

Having regard to the above, it is the object of the present invention to provide a user interface and manner of presentation, as well as methods of operation, which assure one or more of the following: ease of retrieving stored data, easy to learn, intuitive and easy to use, fast to use, ease of entering data, and ease of navigating. It is a further object to provide a user interface including enhanced display/patient notification features, safety features, and/or medical device programming/communication features.

DISCLOSURE OF THE INVENTION

In the disclosure of the present invention, embodiments and aspects will be described which will address one or more of the above objects or which will address objects apparent from the below disclosure as well as from the description of exemplary embodiments.

Thus, in a first aspect a device for displaying information is provided, comprising data storage means for storing data, display means adapted to display data to a user, processor means adapted to control the display means and the data storage means, and user input means. The processor means is adapted to store data organized as data units, each data unit comprising (i) time data, (ii) type data, and (iii) information data. The processor means is further adapted to control the display means to (a) graphically display an aggregate period view comprising at least two period views, (b) graphically display a single period view, (c) graphically display a data type symbol corresponding to a given data type, (d) graphically display at least one data type symbol for every period view, and (e) display a card view comprising information data corresponding to a selected data type symbol. The user input means allows the user to (1) select a desired period view from an aggregate period view, the display means thereby displaying the selected period view, and (2) select a desired symbol from the selected period view, the display means thereby displaying a card view showing at least a portion of the corresponding information data.

By this arrangement a data display user interface is created providing the user with both an overview of stored data, yet allows the user to easily navigate to retrieve more detailed data information as desired, e.g. the aggregate period view may represent a 7, 5 or 3 days and the period view represent a day or a given number of hours. The display may also be adapted to display one or more symbols corresponding to a time line.

The device for displaying information in accordance with the invention may have many different configurations. For example, the device may be a stand-alone device adapted primarily for storing or displaying information, or it may be provided as part of a device providing further functions, e.g. a drug delivery device, a remote controller for a drug delivery system, a blood glucose meter, a mobile phone, or a PDA to mention some exemplary embodiments. The present invention may also be implemented in a handheld or stationary computer device, e.g. in a PC.

The user input means may allow the user to select a card view showing information data of the next or the previous data unit stored in the storage means, the order of the data units being defined by the corresponding time data for the data units.

The display means may be adapted to display a view menu allowing a user to select between two or more types of symbols or combinations of symbols (e.g. for a BG value and a bolus value) to be displayed for a given aggregate period view or a period view. The user input means may then allow the user, for the selected type of symbol or combination of symbols, to select a card showing information data of the next or the previous data unit stored in the storage means, the order of the data units being defined by the corresponding time data for the data units.

In an exemplary embodiment the user input means allows the user to select a first mode in which selected data can be displayed, and a second mode in which data items can be entered using the user input means. The display means may be adapted to display a data entry menu allowing a user to select between two or more types of data, the selected type of data allowing the user to enter data corresponding to the selected type. The input means may be adapted to allow the user to select a period from a displayed aggregate period view, the selected period at least partially determining the time data for the data to be entered, this preventing that the user has to fully enter time data for a given action.

In exemplary embodiments the data unit comprises data from one or more of the following groups of data: (a) type data representing a blood glucose value, time data representing a point of time, and information data representing a blood glucose value, (b) type data representing a meal, time data representing a point of time, and information data representing a value representing a characteristic of the meal, (c) type data representing a bolus delivery, time data representing a point of time, and information data representing a size of a bolus, (d) type data representing exercise, time data representing a point of time, and information data representing a value representing the level of exercise, (e) type data representing one of a change in a basal delivery rate, taking of medication, or illness, and time data representing a point of time. Each type data may be associated with a different graphical symbol adapted to be displayed on the display means.

In a further aspect a drug delivery system is provided, comprising a device for displaying information as described above, a reservoir adapted to contain a drug, an expelling assembly adapted for cooperation with the reservoir to expel drug out of the reservoir, and at least one processor adapted to control the expelling device in accordance with a programmed infusion profile.

Depending on the system configuration the system may comprises one or more processors wherein the different tasks of supporting the user interface and controlling the delivery means may be performed by a single processor or two or more processors in combination.

In the context of the present application and as used in the specification and claim, the term processor covers any combination of electronic circuitry suitable for providing the specified functionality, e.g. processing data and controlling memory as well as all connected input and output devices. A processor will typically comprise one or more CPUs or microprocessors which may be supplemented by additional devices for support or control functions. For example, in case a communication interface is provided (e.g. wireless), the transmitter and receiver may be fully or partly integrated with a processor, or may be provided by individual units. Each of the components making up the processor circuitry may be special purpose or general purpose devices. Correspondingly, the term data storage means covers any combination of electronic circuitry suitable for providing data storage. The term display means covers any type of display capable of visually providing a user with the specified functionality, e.g. a LCD or OLED.

The system may comprise a delivery unit in which the reservoir and the expelling assembly are arranged, and a control unit comprising the display and user input means, the delivery and control units being adapted to communicate with each other, e.g. by wire, RF or IR. Alternatively, the system comprises a delivery unit in which the reservoir and the expelling assembly are arranged, the delivery unit further comprising the display and user input means.

The drug may be in the form of a fluid drug or a powder drug. For a fluid drug the expelling assembly may be in the form of a pump forcing or drawing drug from the reservoir and into a patient through a transcutaneous access device.

For a fluid drug or a powder drug the expelling assembly may also be semi-automatic dispensing a given amount of drug from a reservoir after which a flow of air created by the person using the system will transport the powder drug to the desired location, e.g. the lungs or other portion of the airways.

The reservoir for a fluid drug may be any suitable structure adapted to hold an amount of a fluid drug, e.g. a hard reservoir, a flexible reservoir, a distensible or elastic reservoir. The reservoir may e.g. be prefilled, user fillable or in the form of a replaceable cartridge which again may be prefilled or fillable. The reservoir may also be in the form of a pressurized aerosol container. For a powder drug the reservoir may in the form of a blister or a plurality of individual blisters.

For a fluid drug the system may comprise or be adapted to cooperate with a transcutaneous access device which may e.g. be in the form of a hollow steel needle, a soft cannula in combination with an external or internal introduction needle, or a micro-needle array. The system may further comprise a transcutaneous device unit comprising a transcutaneous access device, and a mounting surface adapted for application to the skin of a subject, wherein the transcutaneous device unit and the delivery unit are adapted to be secured to each other to form a combined device.

The user input means may be in the form of a keyboard comprising one or more user accessible keys, however, alternative a touch display or voice recognition may be used. The user input means may allow a user to e.g. bi-directionally scroll between period views from an aggregate period view, or enter data information by using bidirectional dial up and down keys. The user input means may also be provided by a four-way rocker switch or a four-way joy-stick, this allowing bi-directionally scrolling or setting of values in two directions or for two different types of input.

In a further aspect a method for displaying information is provided, comprising the steps of (A) storing data as data units, each data unit comprising (i) time data, (ii) type data, and (iii) information data, (B) providing display means adapted to (a) graphically display an aggregate period view comprising at least two period views, (b) graphically display a single period view, (c) graphically display a data type symbol corresponding to a given data type, (d) graphically display at least one data type symbol for every period view, and (e) display a card view comprising information data corresponding to a selected data type symbol, (C) selecting a period view from an aggregate period view, the display means thereby displaying the selected period view, and (D) selecting a symbol from the selected period view, the display means thereby displaying a card view showing at least a portion of the corresponding information data. The method may be exercised utilizing a device comprising one or more of the features described above.

As used herein, the term "fluid drug" is meant to encompass any drug-containing flowable medicine capable of being passed through a delivery means such as a cannula, hollow needle or inhalation conduit in a controlled manner, such as a liquid, solution, gel, fine suspension or a powder. Representative drugs include pharmaceuticals such as peptides, proteins, and hormones, biologically derived or active agents, hormonal and gene based agents, nutritional formulas and other substances in both solid (dispensed) or liquid form. In the description of the exemplary embodiments reference will be made to the use of insulin. Correspondingly, the term "subcutaneous" infusion is meant to encompass any method of transcutaneous delivery to a subject.

BRIEF DESCRIPTION OF THE DRAWINGS

In the following the invention will be further described with reference to the drawings, wherein.

In the figures like structures are mainly identified by like reference numerals.

DESCRIPTION OF EXEMPLARY EMBODIMENTS

When in the following terms such as "upper" and "lower", "right" and "left", "horizontal" and "vertical" or similar relative expressions are used, these only refer to the appended figures and not to an actual situation of use. The shown figures are schematic representations for which reason the configuration of the different structures as well as there relative dimensions are intended to serve illustrative purposes only.

The present invention relates to a user input device adapted to cooperate with a drug delivery device (e.g. a drug delivery pump) in a drug delivery system.

Figure 1:
FIG. 1 shows a user input device in the form of a remote control (RC)

FIG. 1 shows a user input device 1 in the form of a remote control (RC) comprising an LCD display 30 arranged at the upper portion of the unit and buttons arranged beneath the display. The placement close to the centre line is chosen for ergonomic reasons. The remote comprises a rocker switch 10 and a left ACCEPT key 21 as well as a right ESCAPE key 22. The rocker switch is the fundamental navigation button and is a four-way switch having four areas 11, 12, 13, 14 supporting respectively the directions: UP-DOWN and LEFT-RIGHT. Indeed, the four areas of the rocker switch may be replaced with a number of keys arranged in any desired configuration. The vertical axis functions to. e.g. (i) scroll up/down in a menu, and (ii) increase or decrease a number. The horizontal axis LEFT RIGHT is used for e.g. (i) scrolling in time, and (ii) changing time related or secondary parameters. The accept button is the fundamental "Yes" button and functions as (i) go forth, enter, select, accept or confirm, and (ii) zoom-in in views. The Escape button is the fundamental "No" button and has the functions (i) no, escape, step back, exit or undo, and (ii) zoom-out in views. Additional functions may be added to the ones described. The display is a dot matrix display and may be a monochrome, greyscale or colour display. The display shows the main screen (MS) which normally is displayed when the RC is turned on. The MS serves to indicate to the user the status of the system controlled by the RC. The screen has a general configuration also used in many other situations of use (see below). More specifically, the MS comprises a central "split screen" area with left and right portions 31, 32 as well as an upper and a lower information bar 33, 34. In the shown view the MS displays in the upper bar the remaining amount of insulin in the insulin pump to which the RC is currently paired as well as the battery status for the RC. The split screen shows the current time and date, and the lower bar shows the current basal infusion rate for the paired pump. Depending on the selected mode of the RC, the split screen can have a "dual mode" configuration (see below) used for a number of input screens.

Depending on the status of the system other information may be displayed, e.g. status indication for an ongoing bolus and/or an ongoing temporal basal infusion rate.

The RC is further provided with an upper port 40 for a build-in BG meter allowing a BG strip to be inserted and a BG value to be determined. The RC may further be provided with one or more keys at e.g. the sides allowing less commonly used functions to be activated, e.g. on-off and keyboard lock. The RC may be powered by replaceable or rechargeable batteries.

Figure 2A:
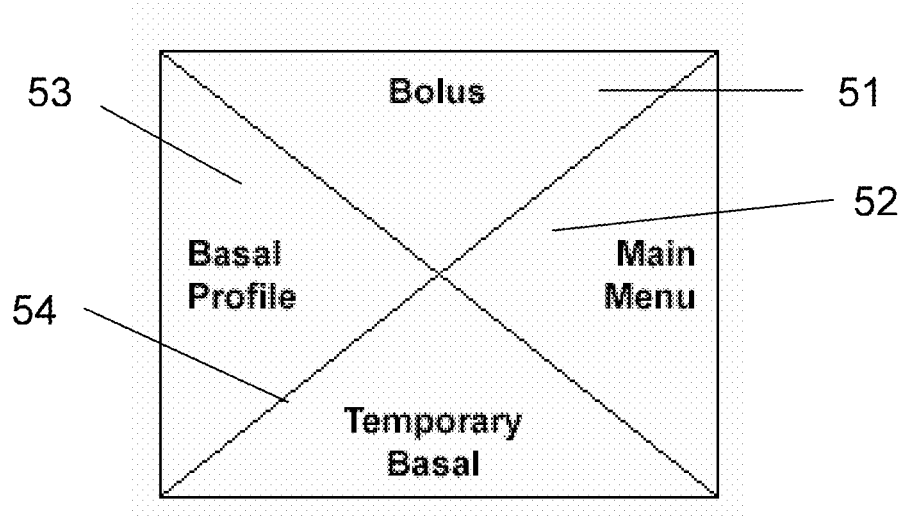
FIGS. 2A and 2B show shortcut menu (SM) respectively main menu (mm) screens for a RC.
Figure 2B:
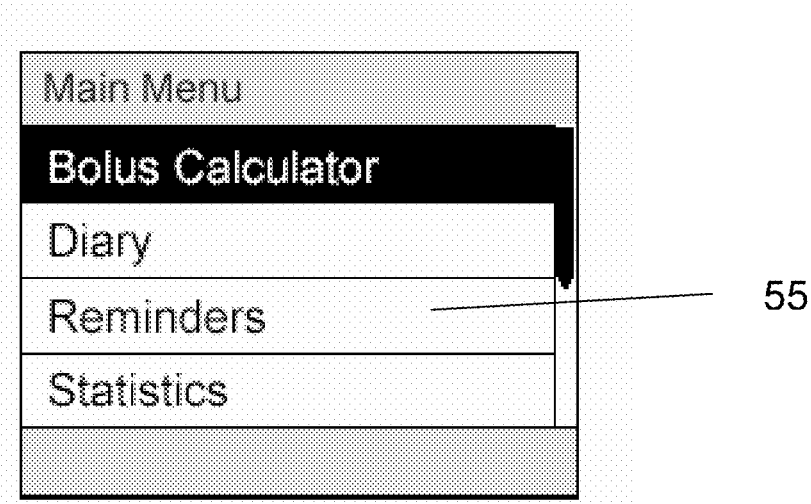

When the remote is turned on it will check whether an initial setup has taken place (e.g. entering personal limits and alarm settings) and if so go to the main or "status screen" as described above. When pressing any key the display will show a shortcut menu (SM) screen having a number of items 51, 52, 53, 54 at predefined locations as shown in FIG. 2A. As described below the text in this screen will depend on the actual bolus condition or basal setting. Using the rocker switch the user can go directly to any of the four indicated items: bolus, profiles, temp (i.e. temporal) basal, or menu screens. When the menu screen is selected a main menu is shown (see FIG. 2B) allowing the user to scroll to a desired menu item 55 and select it, e.g. diary, statistics, reminders or setup. Having a section with a traditional menu makes it easy to add or remove features without breaking up the entire structure. Further, such a menu structure is also makes it easy to provide a customizable interface allowing health care professionals to control how much functionality should be available to a given user. This said, the shortcut menu type of FIG. 2A may be used also for one or more sub-levels of menus, e.g. the four menu items of FIG. 2B may be displayed corresponding to FIG. 2A. One or more of the four sub-level shortcut menus may then be provided with a further level of shortcut menus.

As appears, the four-way rocker switch and the SM screen represents a concrete embodiment of a user input device in which a display is adapted to simultaneously display a plurality of menu items having a predefined location on the display means, and user input means allowing a user to directly select each of the simultaneously displayed menu items. However, as will be explained in detail below, the present user interface provides a high degree of user friendliness by combining the menu selection means (e.g. the rocker key), with a second user interface in which the display means is adapted to display at least one user settable drug delivery parameter, wherein the user input means comprises a keyboard comprising at least one pair of user input keys, each pair allowing a user to bi-directionally set a user settable drug delivery parameter when user controllable settings are displayed.

Figure 3A:
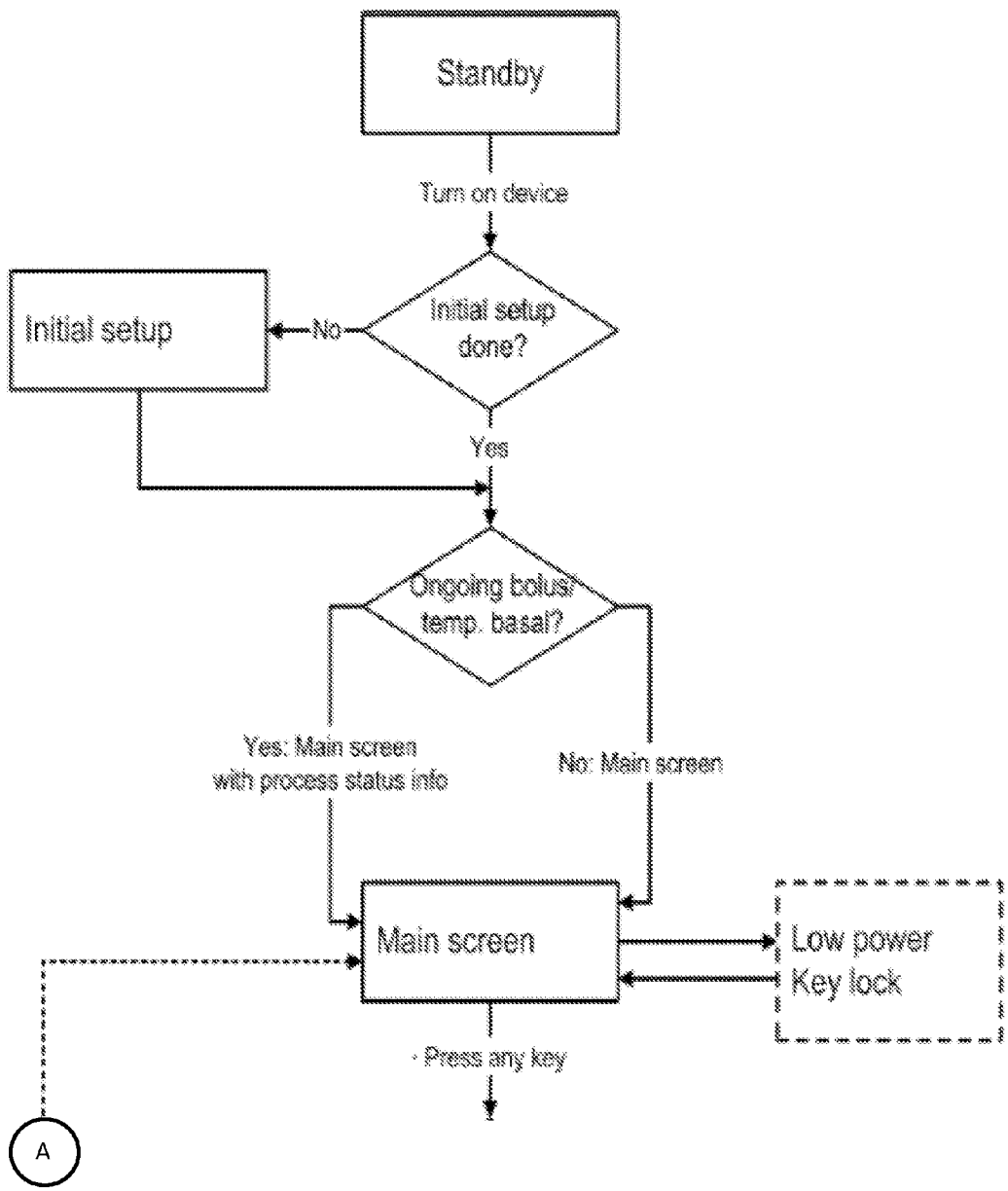
FIGS. 3A and 3B show a flowchart for a RC user interface architecture.
Figure 3B:
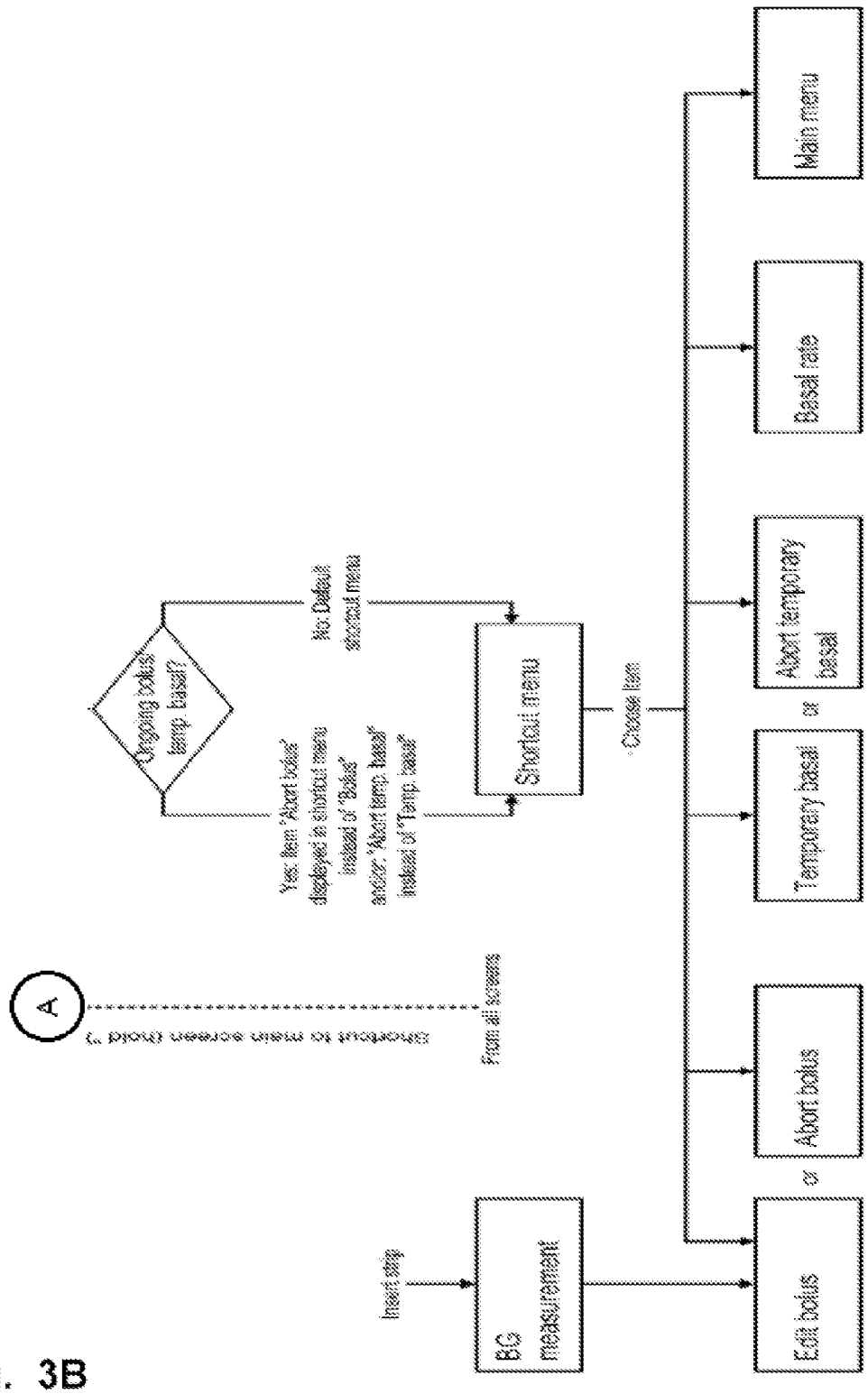

FIG. 3 shows an embodiment for a general user interface (UI) architecture for the remote controller (RC). The UI has a main screen (MS) which normally is displayed when the RC is turned on. The MS may be the standard MS or it may show additional information relating to an ongoing bolus or temporal basal (TB) rate. When the RC is switched on for the first time, the user is guided to the initial setup menu. From the MS the user can by pressing any key go to the shortcut menu (SM) from which the specific main functions can be chosen, either directly or via a main menu (MM). As indicated, an ongoing bolus or TB rate will influence the options in the SM.

Figure 4A:
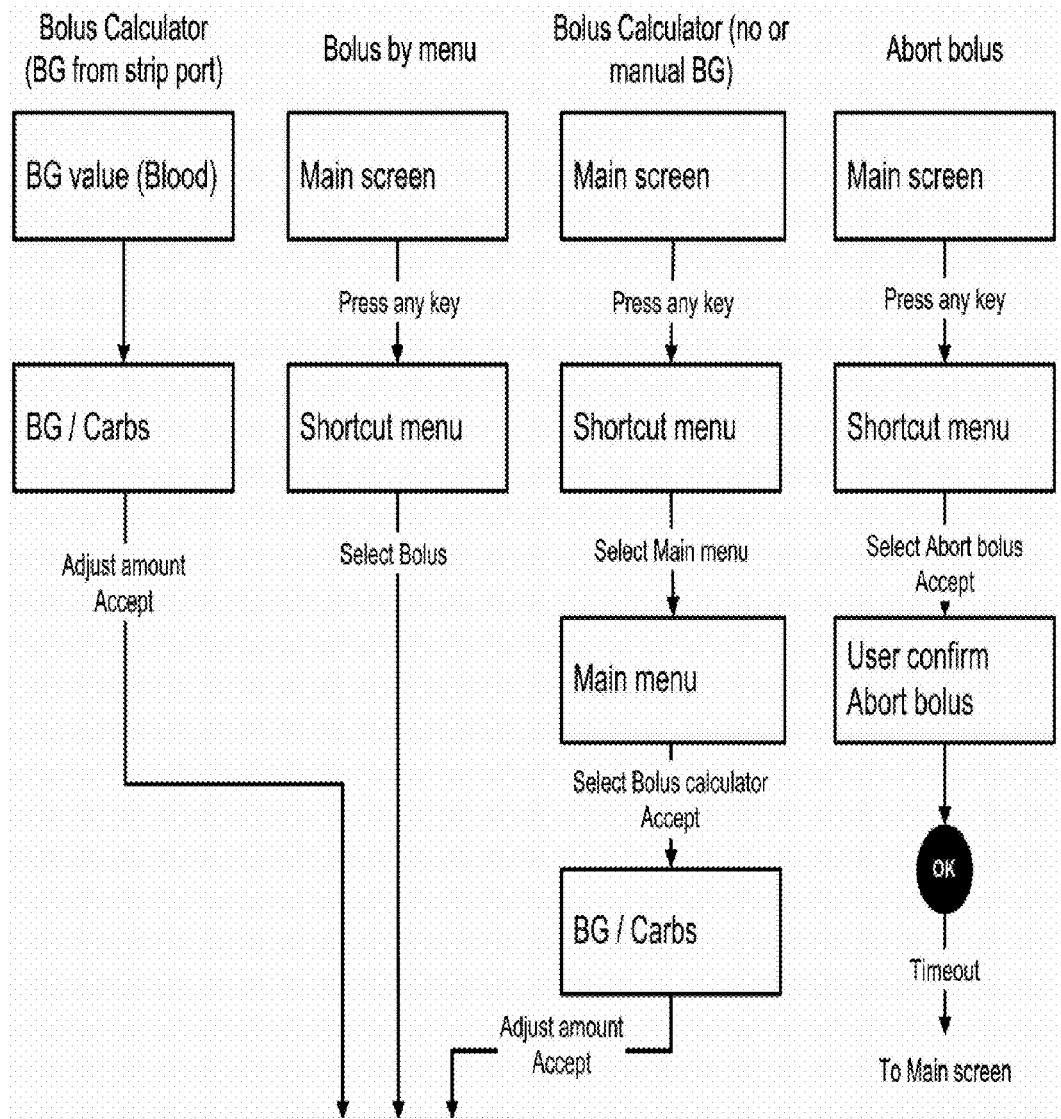
FIGS. 4A and 4B show different paths to an "edit bolus" menu.
Figure 4B:
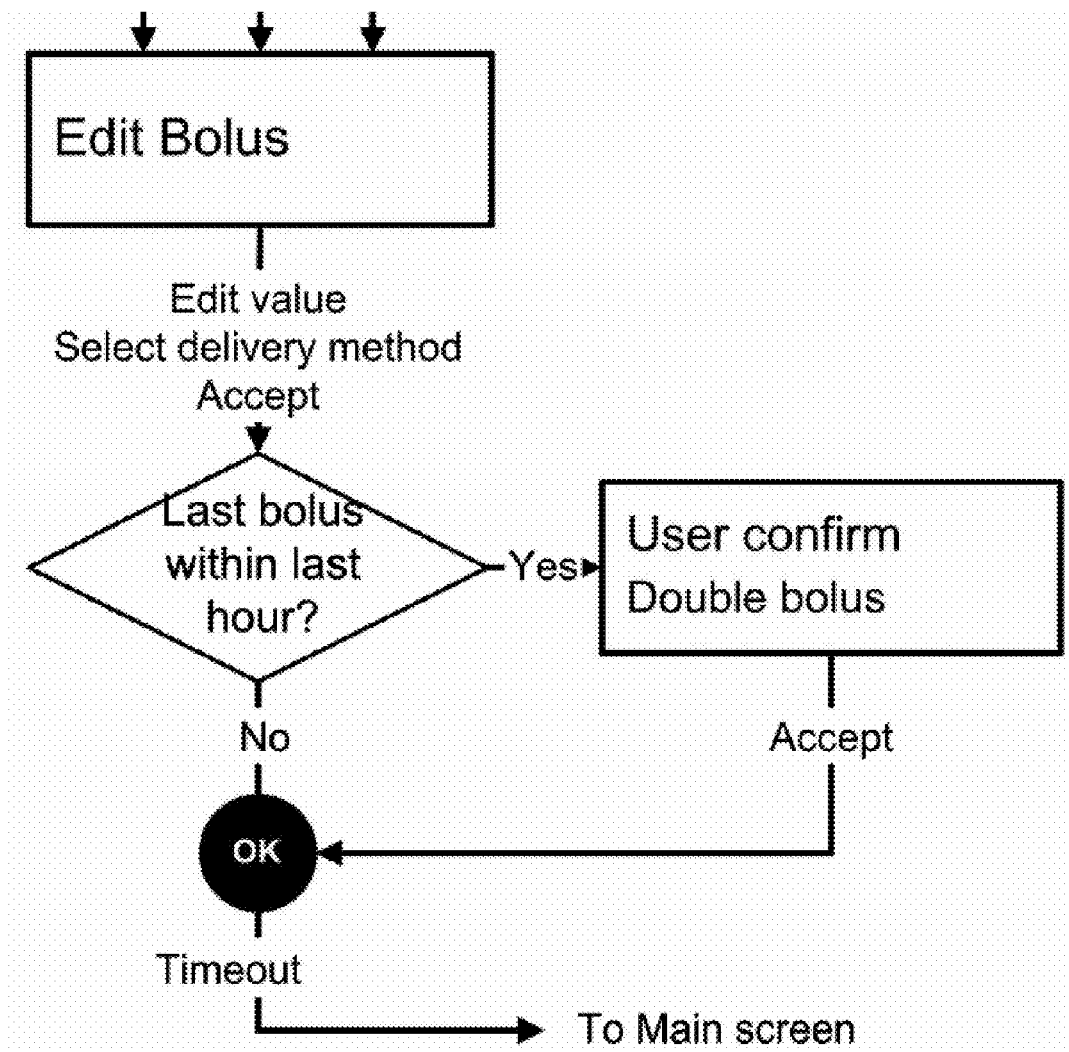

Turning to the individual main functions, FIG. 4 shows how the user can be guided to the "edit bolus" menu in three different ways: (1) after having determined a blood glucose value (BG) using the RC strip port (or alternatively by an external BG meter), (2) directly by the user, or (3) by using the bolus calculator (selected via the MM). In addition, a running bolus can be aborted.

Figure 5A:
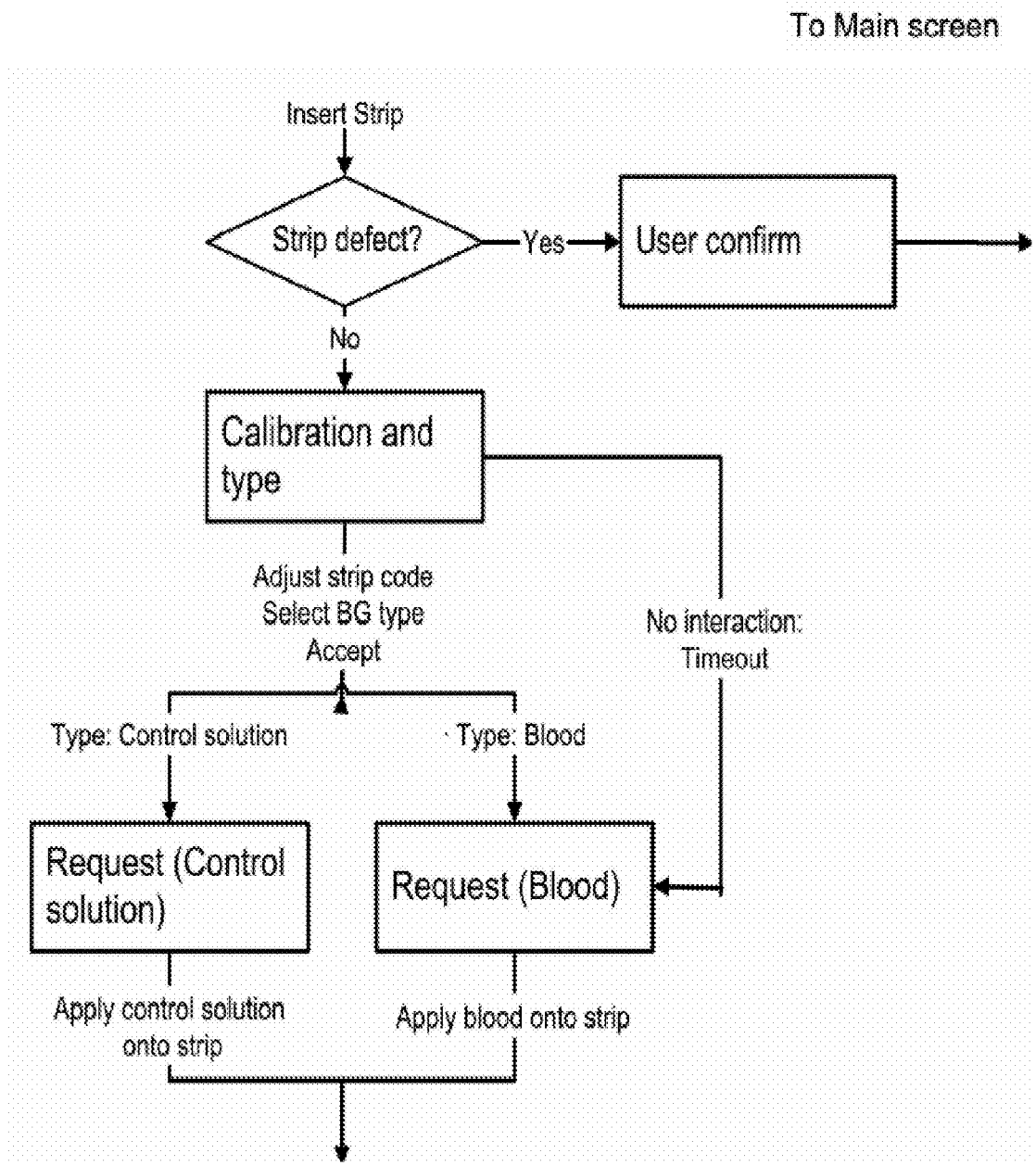
FIGS. 5A and 5B show, use of the build-in BG meter in order to enter a bolus.
Figure 5B:
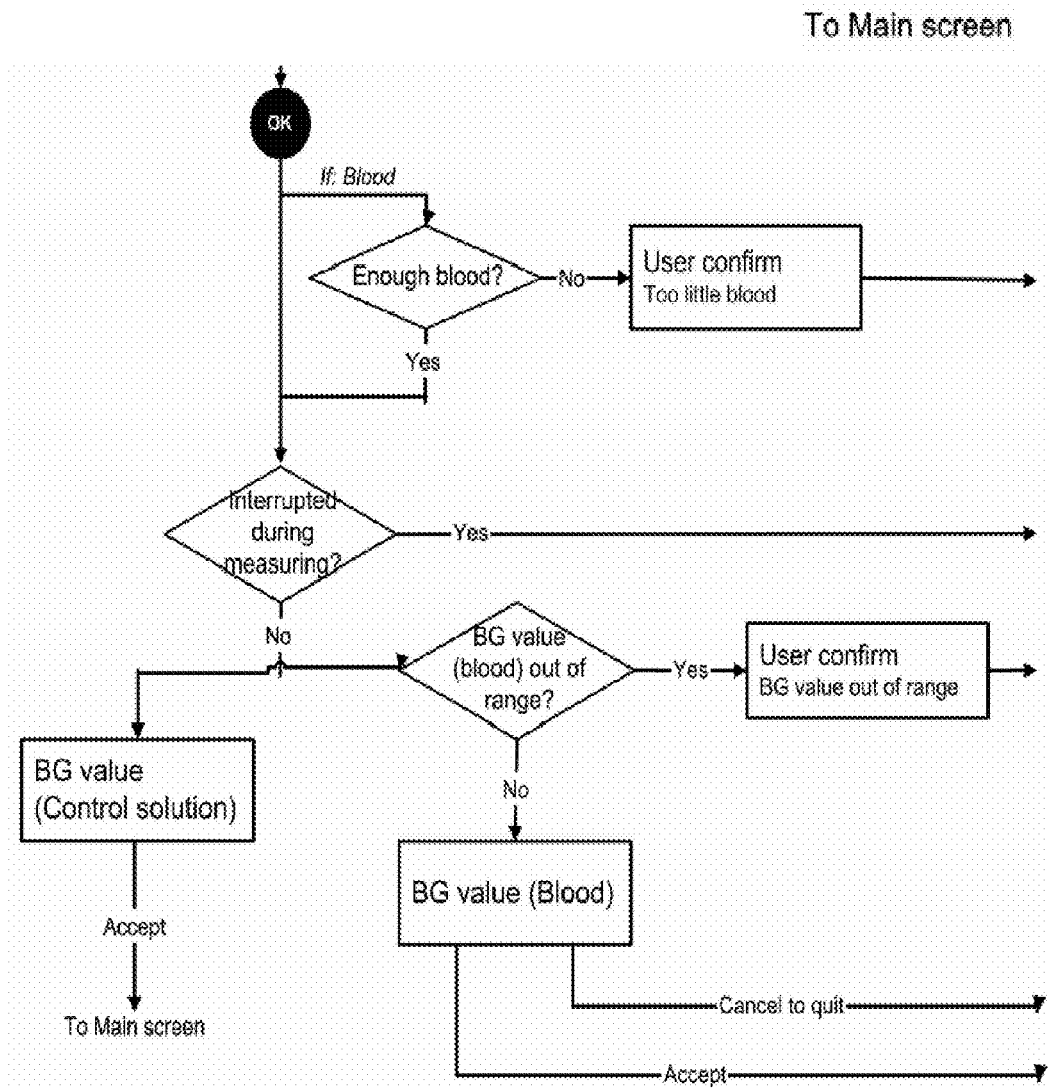

FIG. 5 shows how the build-in BG meter is used and how it can be used to enter the bolus menu. When a BG strip is inserted the user is asked for calibration and type data, however, with no input the RC swiftly proceeds to the "request blood". If a sufficient amount of blood is placed on the strip and a BG within the set normal range is produced and displayed, the user is offered the option to go to the bolus calculator or leave the BG menu. If the bolus option is chosen the user is requested to enter meal carbohydrates (if any) and the RC will calculate and display a suggested bolus size. The user can then use this information as guidance when freely setting a bolus of a desired size.

Figure 6:
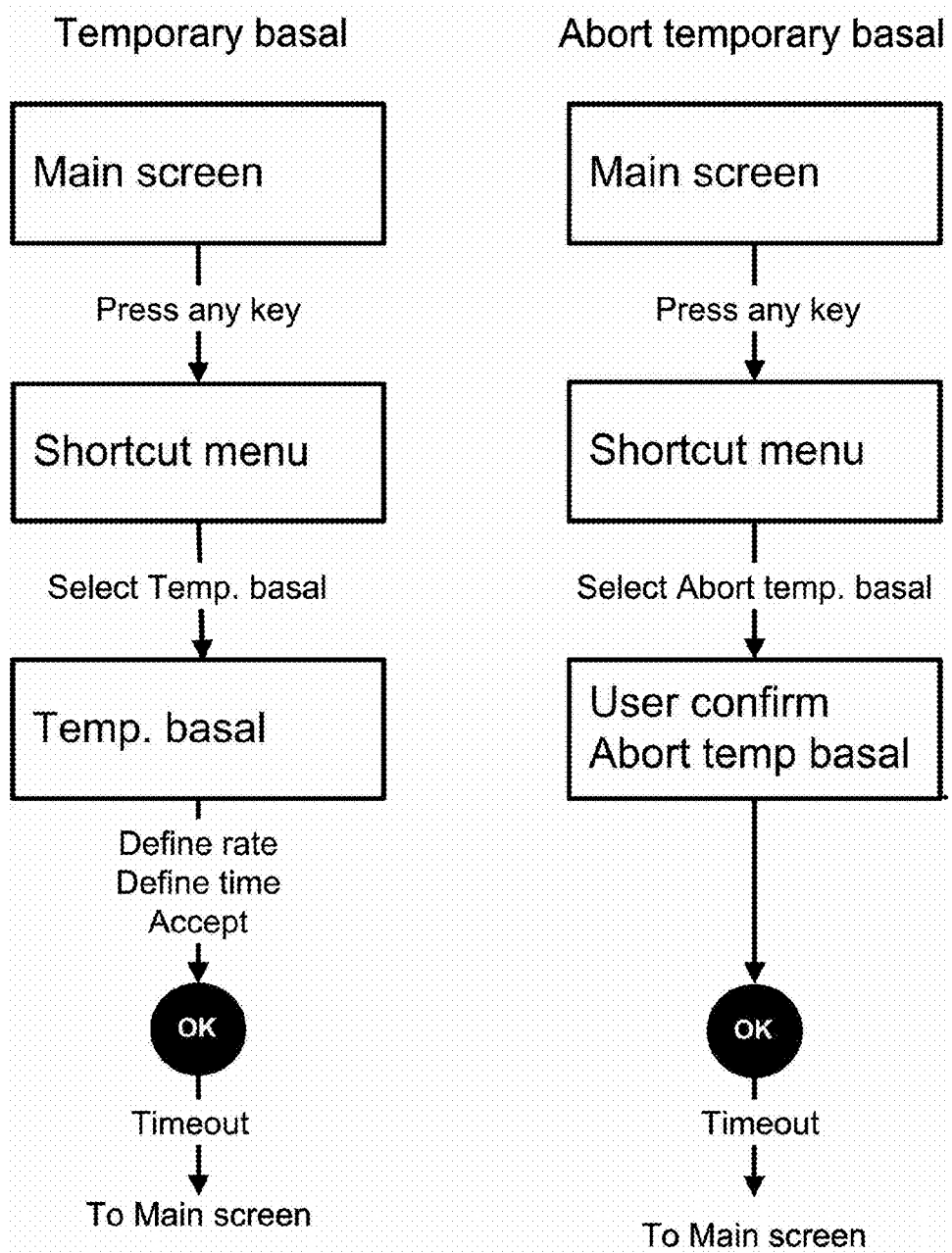
FIG. 6 shows temporal basal (TB) options by which the user can set or cancel a TB.

FIG. 6 shows the two TB options by which the user can set or cancel a TB. How to set a temp basal is described below with reference to FIG. 13.

Figure 7A:
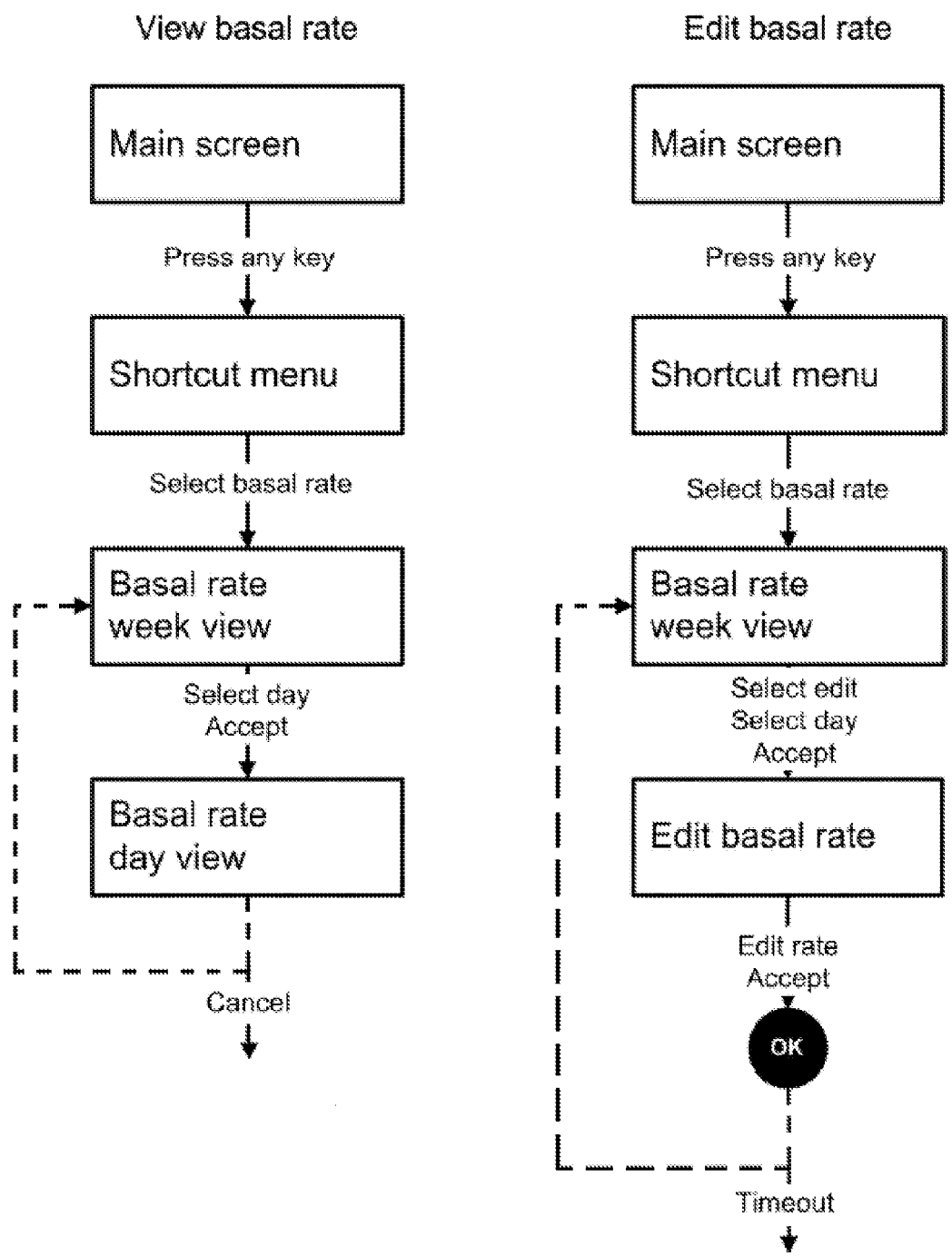
FIGS. 7A and 7B show how the user can view, edit or redefine the basal rate (BR)
Figure 7B:
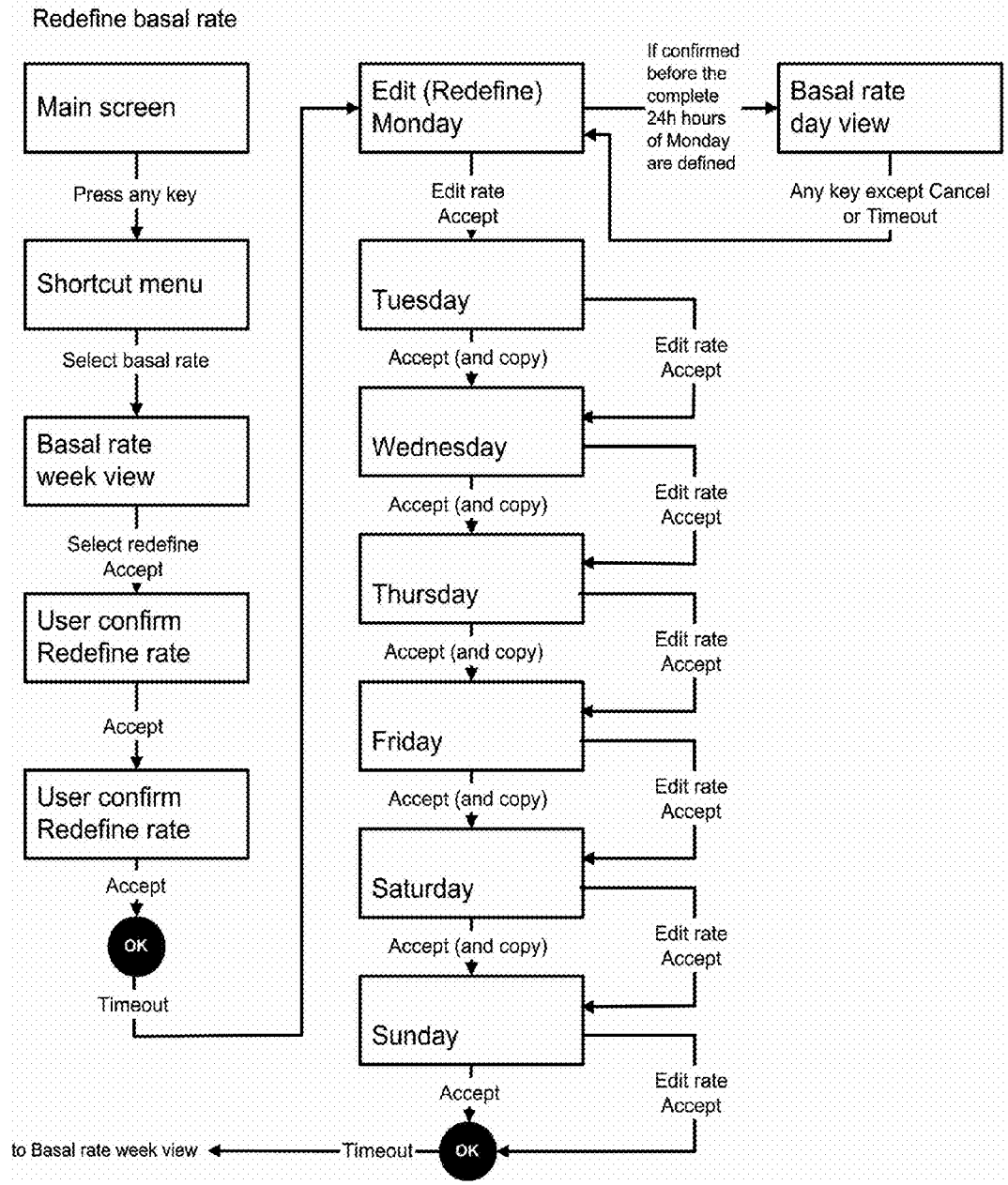
Figure 17:
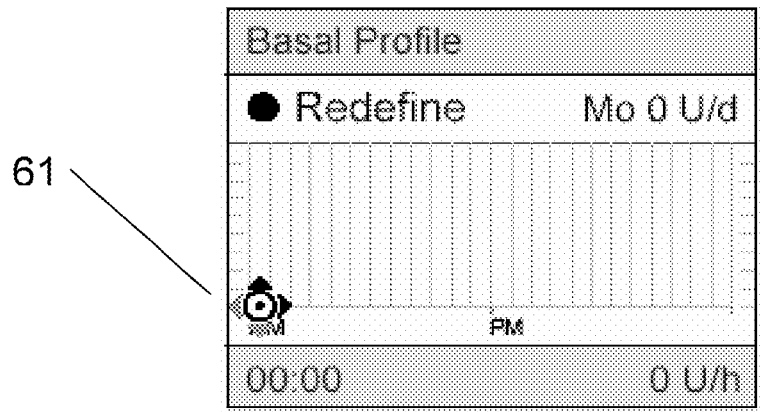
Figure 18:
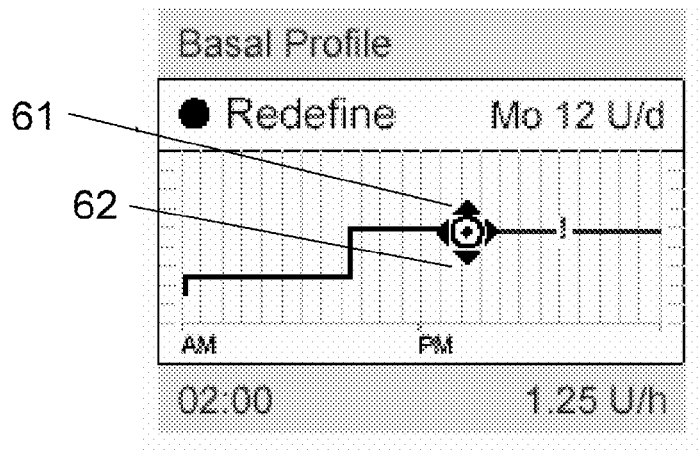

FIGS. 7A and 7B show how the user can either: (1) view the basal rate (BR) profile, (2) edit the BR profile, or (3) redefine the BR profile. Instead of a recurring one-day BR profile the disclosed system uses a 7-day BR profile which is set for the first time during the initial set-up. Via the "edit BR profile" function the user can select a single day and change the BR profile of that day. Alternatively, the user can decide to re-set the entire 7-day profile. If the profile is the same for every day, once the first (e.g. Monday) BR profile is entered, the user can copy the profile for the subsequent days. How to set a daily BR profile is described below with reference to FIGS. 17 and 18.

In the MM the user can select between "bolus calculator" (see above), "diary" (in the flow charts also named "log book"), "reminder", "statistics" and "setup".

Figure 8A:
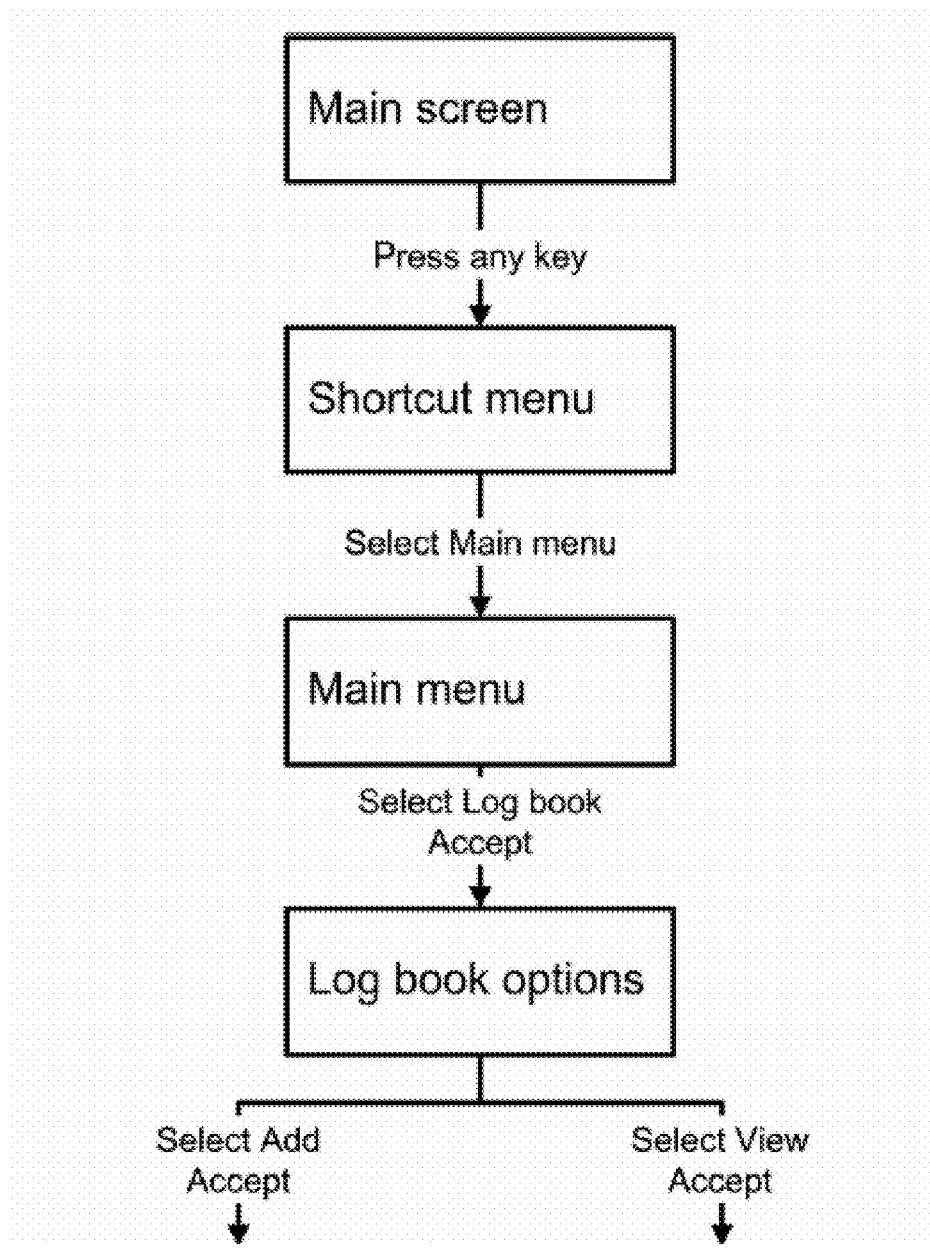
FIGS. 8A and 8B shows the options available to the user for the diary function.
Figure 8B:
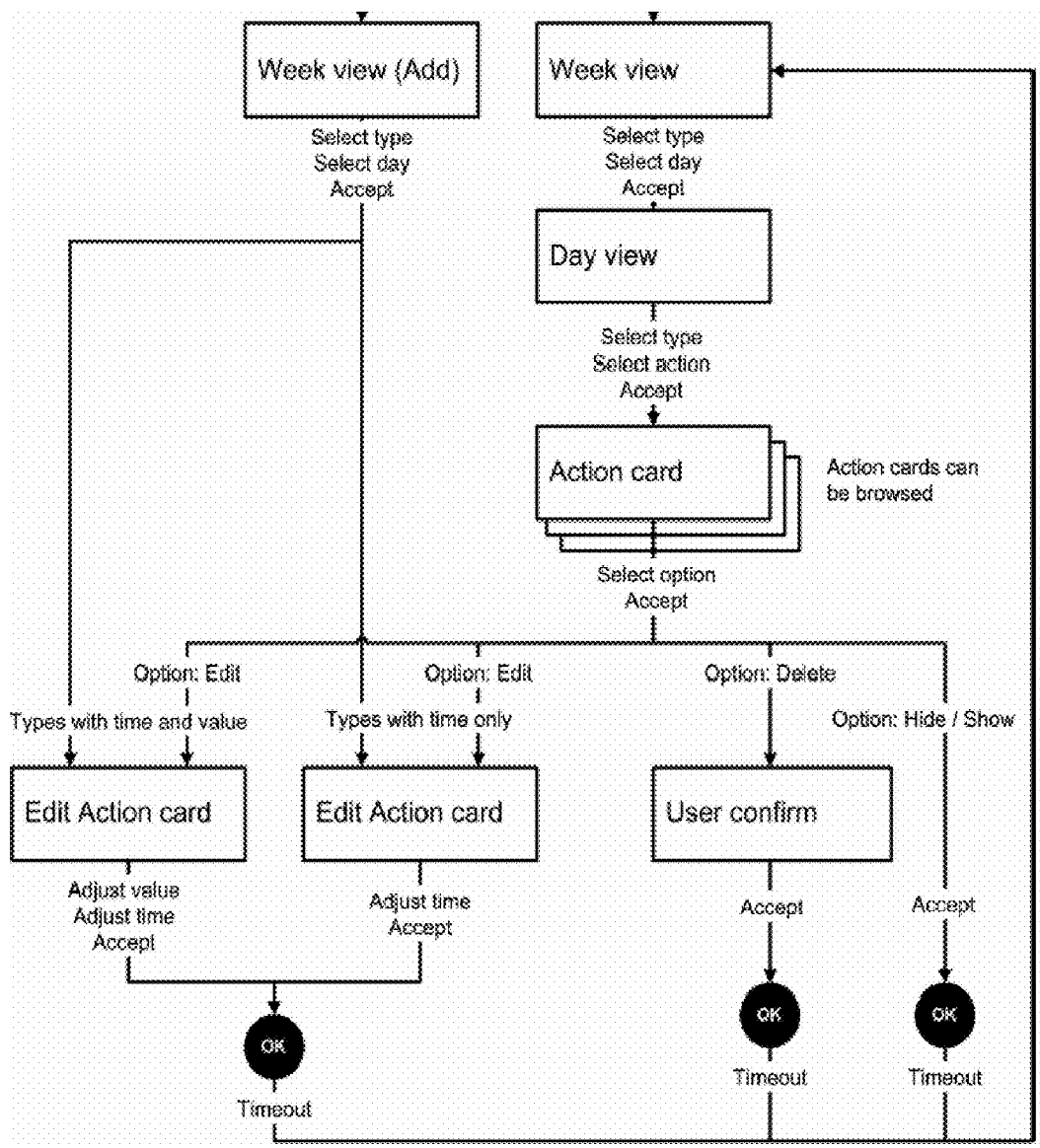

FIG. 8 shows the options available to the user for the diary function. In the "view" option the display opens with a 7-day view showing a pre-selected type of information, e.g. BG values, or combination of types of information, e.g. BG values and bolus. For a given type of information, each event is represented by a specific icon. The user now has to two options, either to select another type of information to be displayed or select a day view showing essentially the same information but in a higher resolution over the 24 hours of the day. The user can also select a different type of information when in the day view state. When in the day view the user can select any of the displayed icons by browsing and then request the associated detailed information to be displayed in an "action card" view. When an action card is displayed the user can browse through the previous or next card for the selected type of information, both for the selected day but also for the previous or subsequent day. When a given action card is selected the user can choose (if allowed) between different options for the displayed information: edit, delete or hide. In the "add" option the user selects a day and a type of information. The user is then presented with an "edit action card" view allowing the user to enter the relevant type of information for the selected type of information, e.g. meal size and time.

Figure 9A:
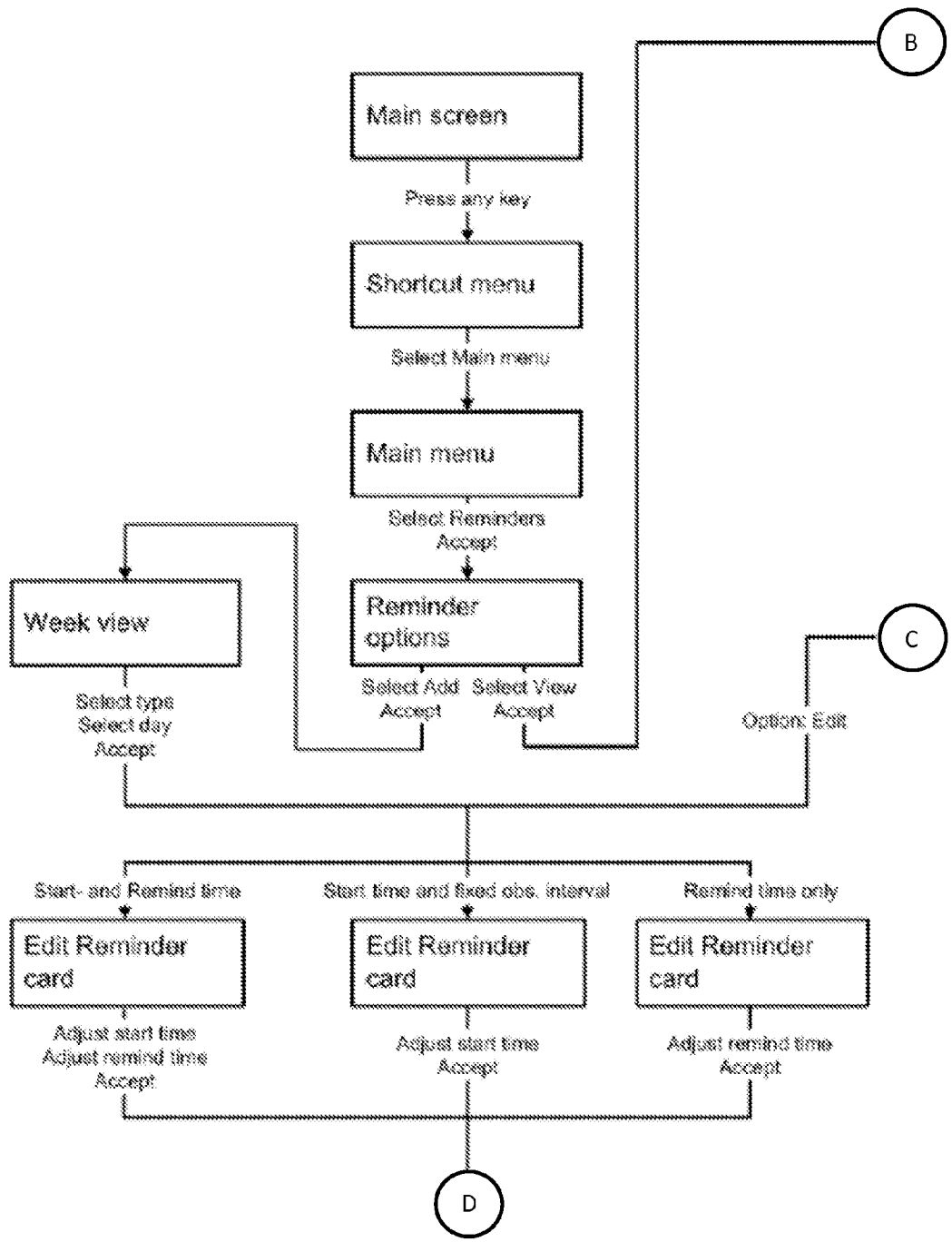
FIGS. 9A-9C show the options available to the user for the reminder function.
Figure 9B:
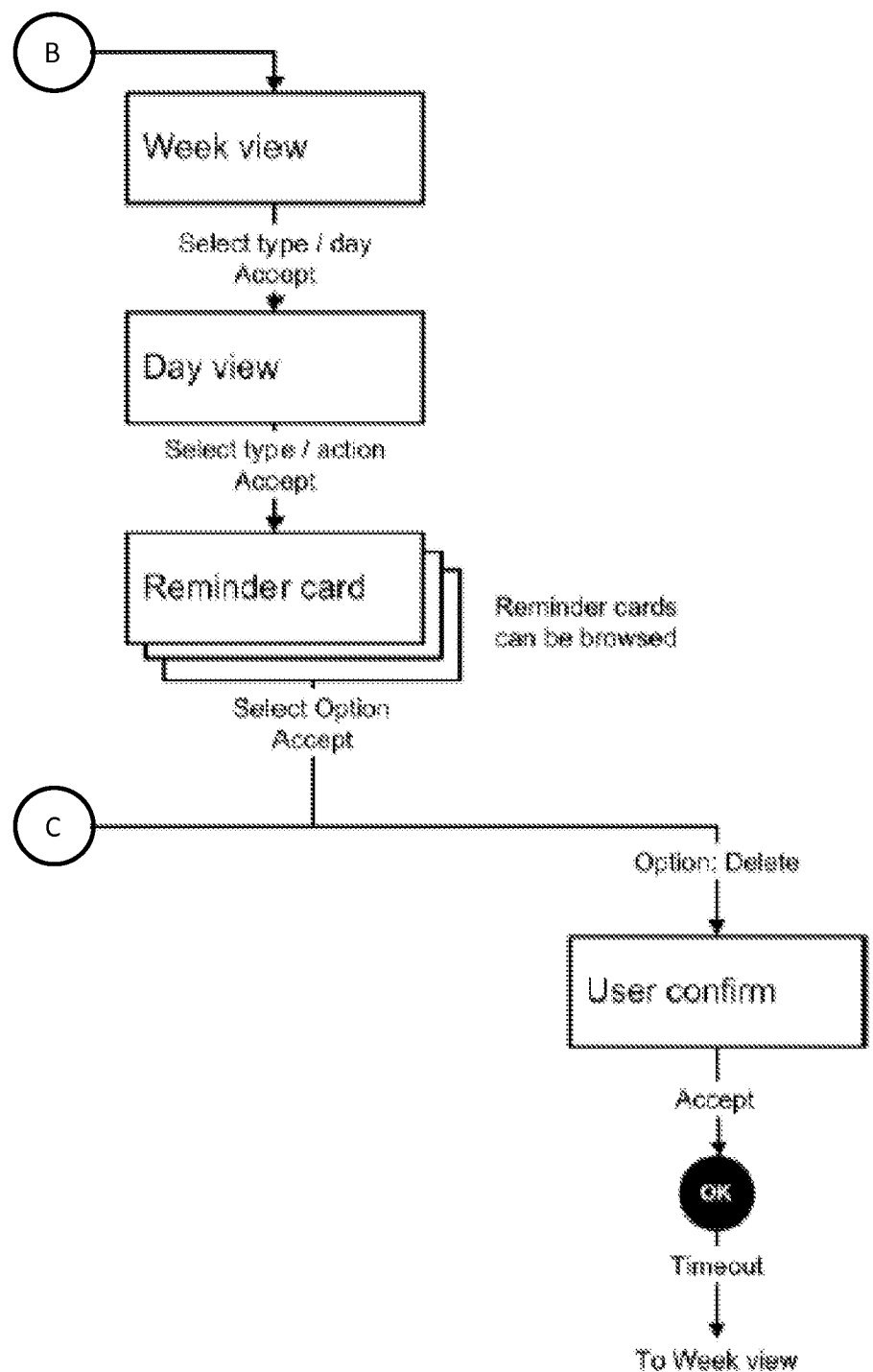
Figure 9C:
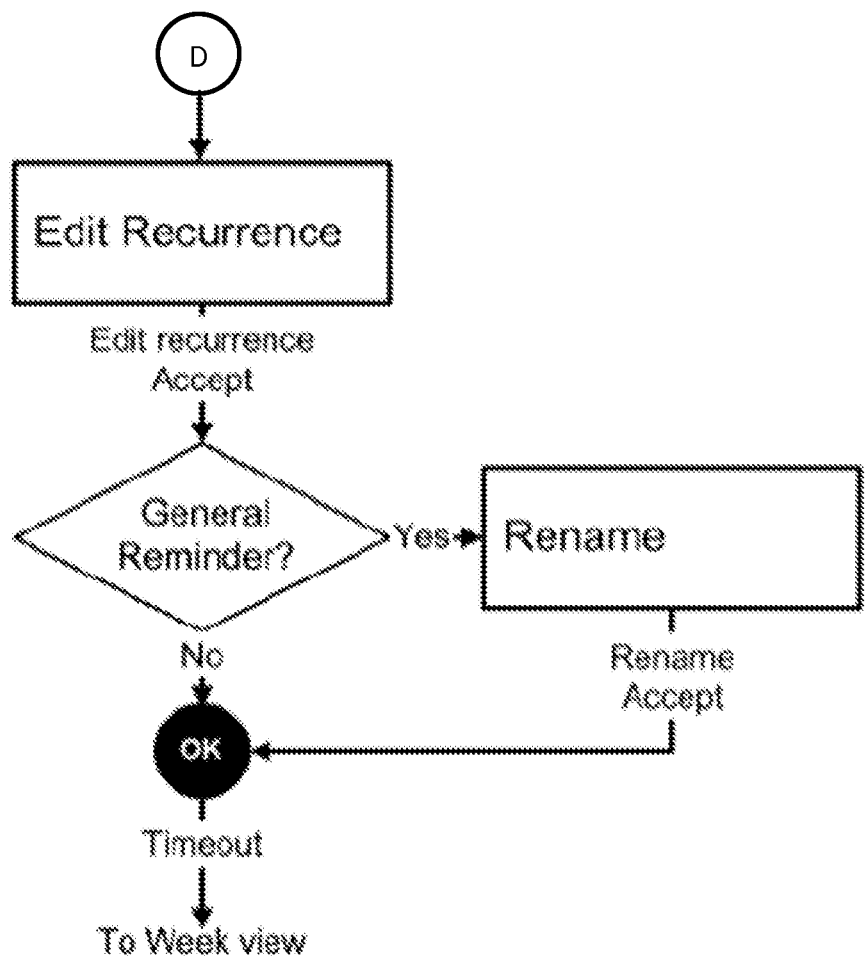

FIG. 9 shows the options available to the user for the reminder function. The reminder function works essentially the same way as the diary function, i.e. the user is presented with week view, day view and "reminder card" (instead of action card) options as well as type of reminders. Correspondingly, the user can edit and add reminders as set out above for the action card information. In addition, when setting a new reminder, the user has a recurrence option, i.e. daily or weekly.

Figure 10:
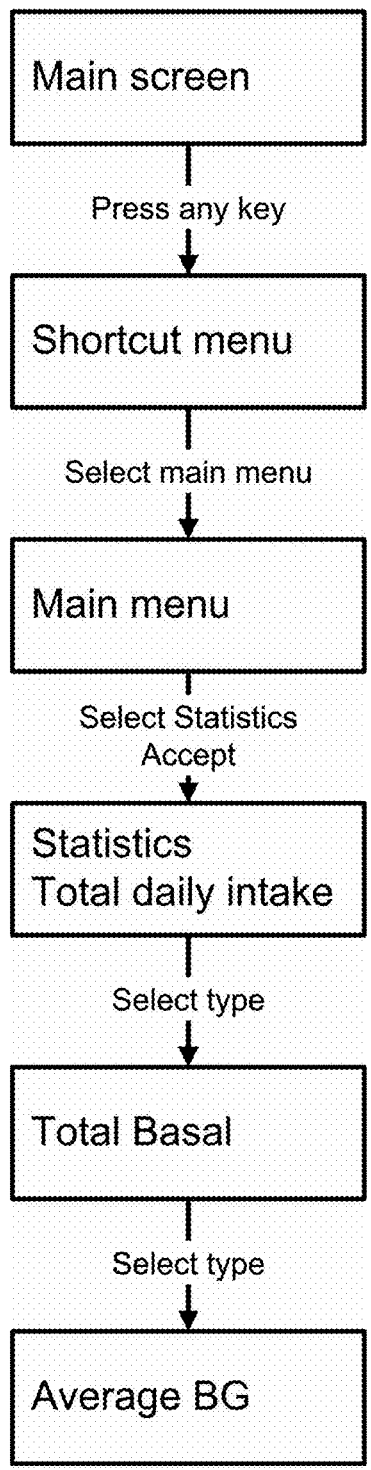
FIG. 10 shows the options available to the user for the statistics function.

FIG. 10 shows the options available to the user for the statistics function. The statistics function can display one or more average values, e.g. for 14 or 30 days, for a selected type of information, e.g. daily basal or daily bolus.

Figure 11A:
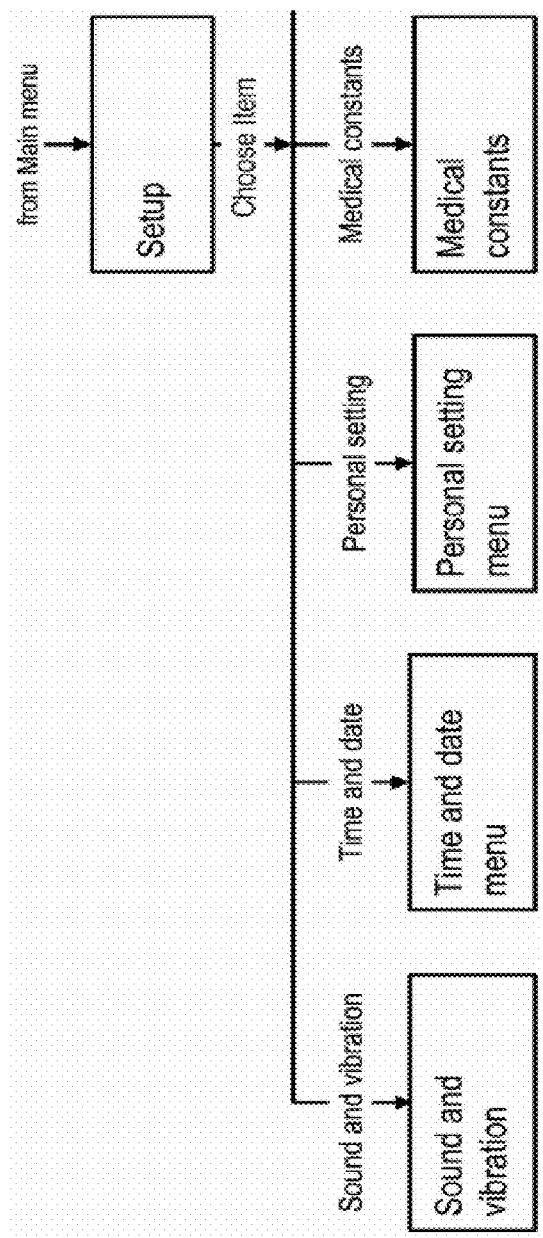
FIGS. 11A and 11B show the different set-up options.
Figure 11B:
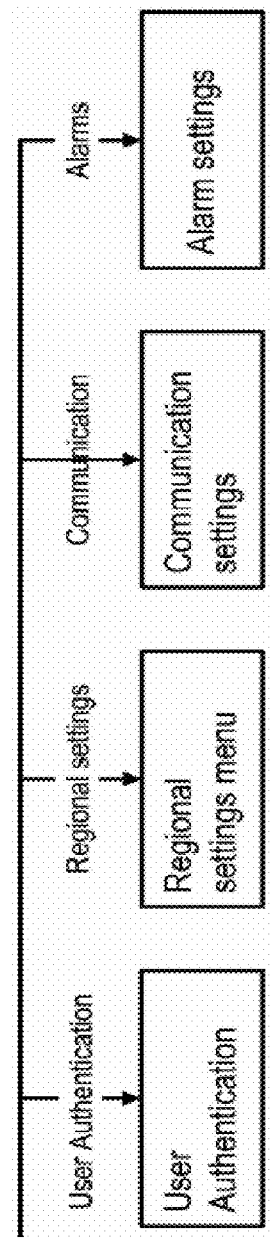

FIG. 11 shows the different options available to the user for the setup function, e.g. time and date, regional settings and alarms.

Figure 23:
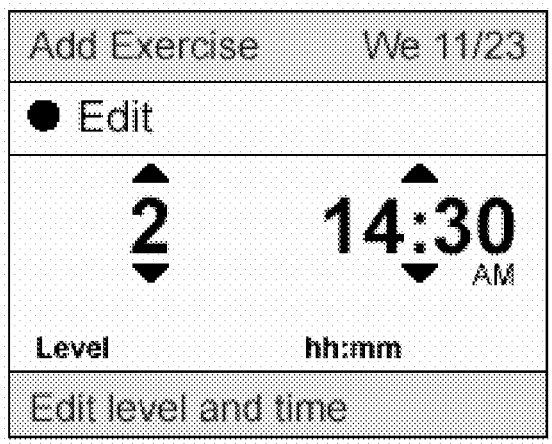

As described with reference to FIG. 29 the pump is controlled via the RC, this allowing new settings to be transmitted to the pump, however, the communication is two-way allowing also the pump to transmit information to the RC, e.g. alarms. Especially for the latter, it is important that communication is upheld between the two units. As shown in FIG. 23, when communication is lost for more than a first predetermined amount of time, e.g. 10 minutes, a first "connection lost" warning will appear in the main screen. If communication is not re-established within a second predetermined amount of time, e.g. 2 hours, a second "connection lost" warning will appear in the main screen and an audible and/or tactile alarm will be sounded.

In the following some of the input options will be described in order to illustrate different user oriented aspects of above described user input device.

Figure 13:
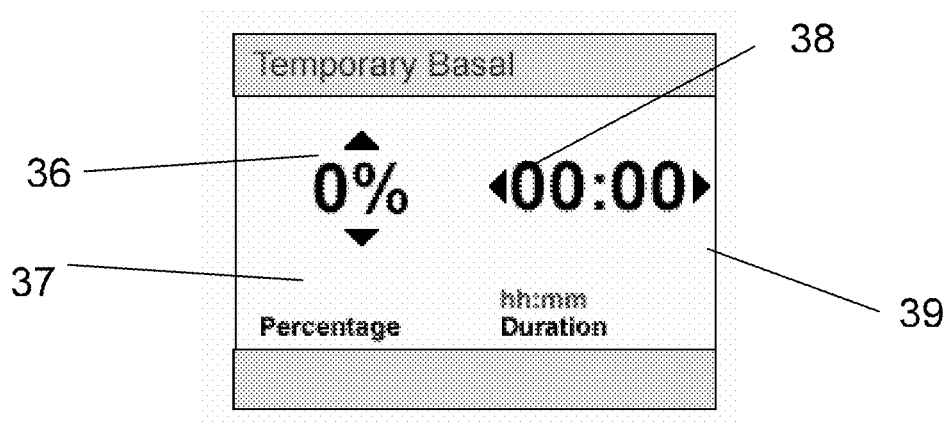
FIG. 13 shows how a TB rate is programmed using a dual-mode screen.

When the user desires to directly enter a bolus to be infused, i.e. without using the bolus calculator, the bolus menu point in the SM is selected by using the UP key which brings the user to the set bolus input screen which is of the "dual mode" configuration, see e.g. FIG. 13. A dual mode screen displays two user controllable settings, e.g. two parameters, which at the same time (i.e. using the same screen) can be directly set by the user using a keyboard provided on the remote. In the present embodiment a four-way rocker switch is provided allowing two settings 65, 66 to be controlled in an "up-down" or scrolling fashion. As can be seen, on the screen image two set of arrows 36, 37, 38, 39 are provided to assist the user when operating the four-way switch. As two different settings can be controlled as well as displayed at the same time a user interface providing ease and safety of use is provided. The display further comprises an upper and a lower bar for additional information.

Figure 12:
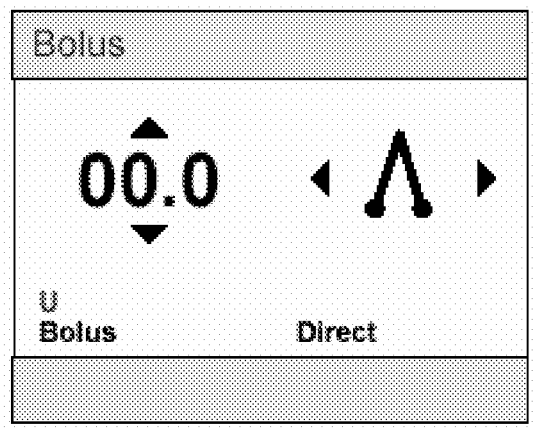
FIG. 12 shows a dual-mode bolus input screen.

More specifically, the bolus input screen in FIG. 12 shows to the left a numerical value (initially showing 0.0) indicating the selected amount of e.g. insulin unit and associated with a set of UP-DOWN arrows. To the right is shown a symbol indicating the selected type of bolus infusion, e.g. "direct" (e.g. as fast as possible), "extended" or "sawtooth" (also called dual-phase), and an associated set of LEFT-RIGHT arrows. As follows, when setting a bolus the user enter the amount of drug using the UP-DOWN keys, and selects the type of infusion by scrolling in the "type menu". To activate the desired bolus ACCEPT is pressed which is then followed by a checkmark on the screen, this indicating that the pump unit has confirmed that the instruction has been received and will be performed, where after the remote automatically returns to the status screen now indicating bolus (remaining time and insulin-amount) as long as bolus is being delivered. In the lower bar a bolus suggestion may be displayed if the edit bolus screen has been entered via the bolus calculator.

When the user will cancel a running bolus infusion using the SM screen is selected which now display "abort bolus" instead of bolus. The user selects the "abort bolus" menu item and confirms abortion by pressing ACCEPT.

Figure 14:
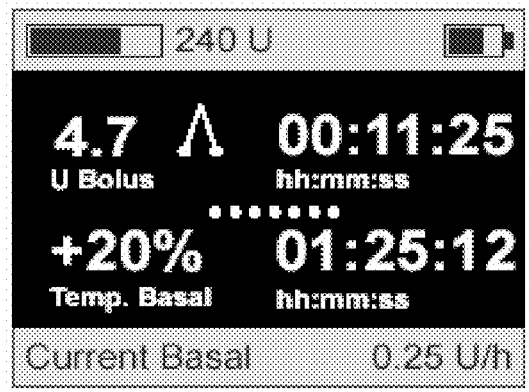
FIG. 14 shows a status screen indicating that both a bolus and a TB rate are being delivered.

FIG. 13 shows another use of the dual-mode screen in which a TB rate is programmed. More specifically, the TB input screen shows to the left a numerical % value 65 (initially showing 0%) indicating the selected percentage adjustment of the running basal rate or profile, and an associated set of UP-DOWN arrows. To the right is shown the selected duration of time 66 for the TB expressed in hours and minutes, and an associated set of LEFT-RIGHT arrows. As follows, when setting a TB rate the user enters the percentage adjustment, selectable from e.g. (−100) % to (+100) % as well as the desired time period for the TB rate. To activate the desired TB rate ACCEPT is pressed which is then followed by a checkmark on the screen, this indicating that the pump unit has confirmed that the instruction has been received and will be performed, where after the remote automatically returns to the status screen now indicating the TB rate in a split screen view (percentage change and remaining time) as long as TB rate is being delivered. FIG. 14 shows a status screen indicating that both a bolus and a TB rate are being delivered.

Using the programming of a new BR profile as an example, FIGS. 15-18 show further types of dual-mode screens. In either the initial setup or in case it is desired to redefine the BR profile the user is brought to a "define profile" screen.

Figure 15:
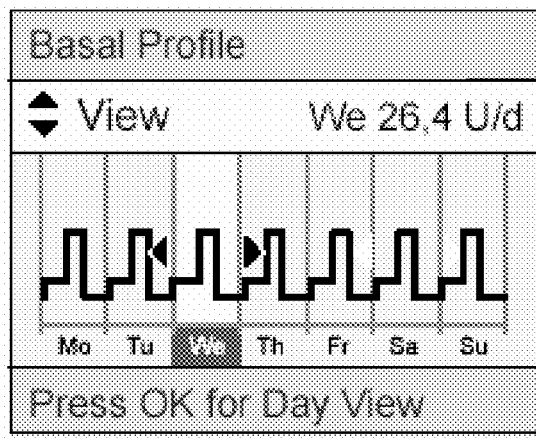
FIGS. 15-18 show further types of dual-mode screens.
Figure 16:
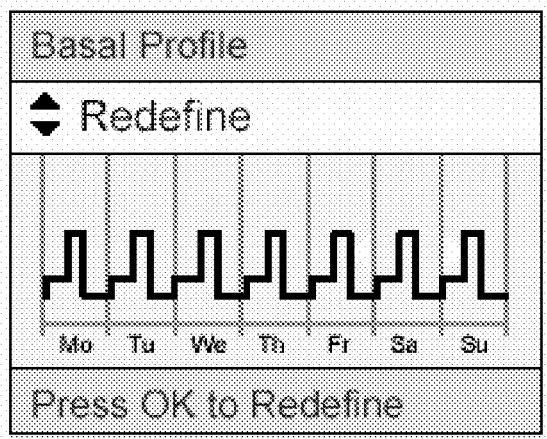

More specifically, when actuating the "basal profile" in the SM the user is brought to a "week view" screen for the BR profile, see FIG. 15. This screen comprises two sets of arrows, a first set being used in a "spinner bar" 35 arranged below the upper information bar, the second set being used for a given selected day. Using the corresponding UP-DOWN keys on the RC the user can toggle between the options in the spinner bar, e.g. "view", "edit" or "redefine". Correspondingly, using the LEFT-RIGHT keys the user can select a given day. When "redefine" is selected (see FIG. 16) the second set of arrows disappears as in the shown embodiment the BR profile can only be redefined for an entire week. Thus, when pressing ACCEPT the user is taken to the redefine BR profile screen, see FIG. 17.

In accordance with an aspect of the invention, the edit BR profile screen is adapted to graphically display an infusion profile showing an infusion rate as a function of time. The profile comprises a number of consecutive segments, each segment indicating a period of time and an associated infusion rate (BR). In the shown embodiment 24 segments are used for a 24 hours period and the profile is shown as a full line. The screen further shows an indicator 61 (here a circle with a dot) arranged corresponding to a given infusion rate for a given point of time, initially a time 0 and indicating an infusion rate of 0 The indicator is associated with two sets of arrows indicating that the indicator can be moved up-down corresponding to a desired BR as well as forth-back corresponding to a desired segment, i.e. desired point of or time. Using the rocker switch the RC is thus provided with first user input means allowing the user to move the indicator corresponding to a desired point of time, and second user input means allowing the user to move the indicator corresponding to a desired infusion rate, whereby the user graphically can draw a continuous profile 62 for a desired period of time by moving the indicator on the screen corresponding to the desired period of time, the drawn profile graphically displaying the BR profile. The actual time and BR corresponding to the indicator is shown in the lower bar. When the profile is completed the user presses ACCEPT, however, if the profile is not completed this will be indicated, e.g. by the "missing" profile portion blinking, see FIG. 18.

In the disclosed embodiment of the RC the BR profile is defined as a 7-day profile. When the first days (e.g. Mondays) profile is programmed, accept of the profile will bring the user to a screen for the next day showing a "pre-set" identical profile which can then be accepted (and so forth until completion of the week), this being expedient as the profile is often the same for a number of day or even all 7 days of the week. In case it is not desirable to copy a profile for the next day, the user simply start to redraw a new profile or change the profile for the previous day.

Next, with reference to FIGS. 19-23, aspects of the diary function will be described, this function providing further implementations of a dual-mode screen.

Figure 19:
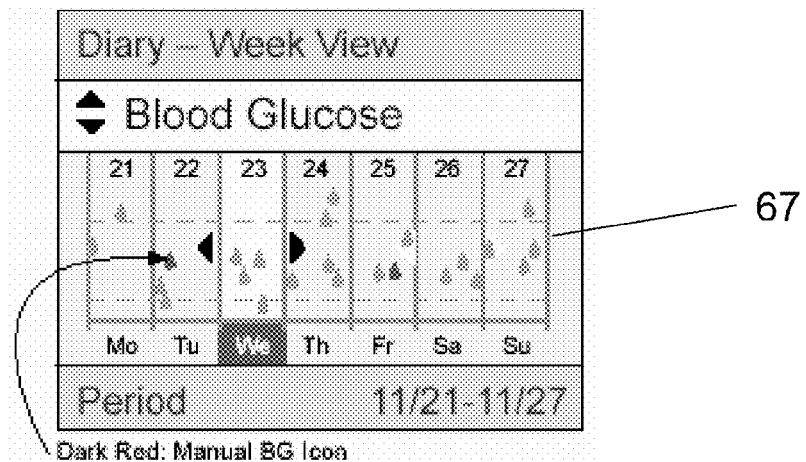
FIGS. 19-23 show aspects of the diary function.
Figure 20:
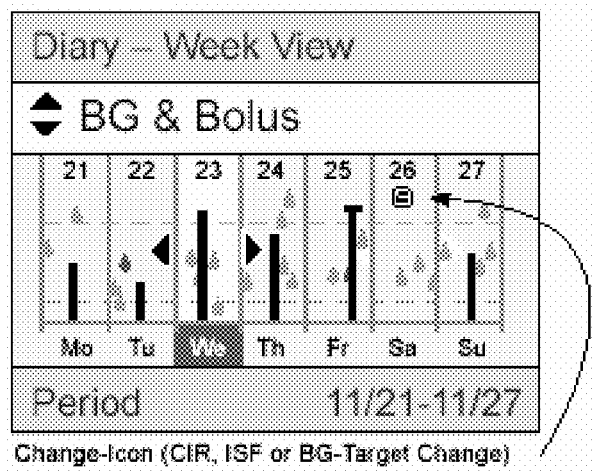
Figure 21:
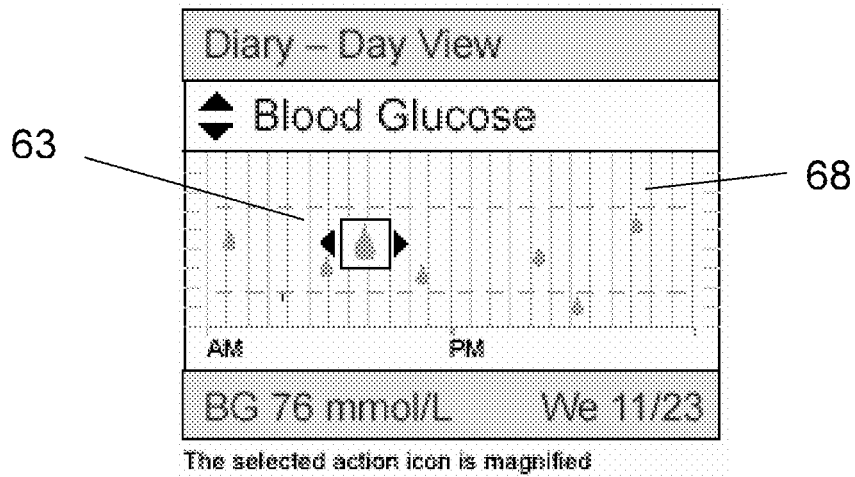
Figure 22:
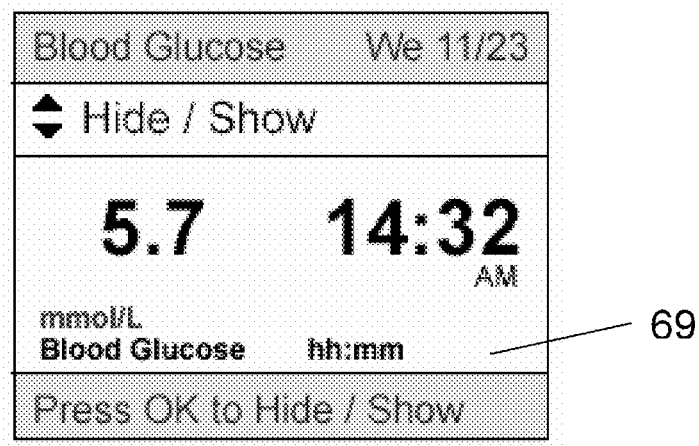

More specifically, using the MM the user selects the diary function which via a view/add "diary-options" menu brings the user to the "diary-week view" screen, see FIG. 19. This screen is similar to the above-described week view for the basal profile, see FIG. 15, i.e. comprising a spinner bar and week view 67 with selectable days, both being selectable using the two sets of keys provided by the 4-way rocker key. Using the UP-DOWN keys the user can select between the following diary item options to be displayed: Blood glucose (BG), BG and bolus (see FIG. 20), BG and basal (i.e. BR profile), and miscellaneous. The diary item options can represent either a single type of data, e.g. BG, or a combination of one or more data types, e.g. BG and basal. Also the miscellaneous item can comprise a number of data types, e.g. meal, medication or exercise. Using the LEFT-RIGHT keys and subsequently the ACCEPT key the user can select a day view 68, see FIG. 21. Both in the week and day view the individual data units are represented by a symbol 63, e.g. for BG a drop or blood, or for basal a change in the displayed profile. When in the day view the second set of arrows is used to indicate a single symbol, the LEFT-RIGHT keys allowing the user to scroll back and forth to previous or next symbol, this including the symbols of the "neighbouring" days. Using the ACCEPT key for a given selected symbol, the user is brought to a "diary action card" screen 69 displaying data associated with the selected symbol, see FIG. 22. A given symbol and its associated data can be considered a data unit which may comprise data from one of the following groups of data: (i) a symbol representing a blood glucose value, time data representing a point of time, and a blood glucose value, (ii) a symbol representing a meal, time data representing a point of time, and a value representing a characteristic of the meal, (iii) a symbol representing a bolus delivery, time data representing a point of time, and a size of a bolus, (iv) a symbol representing exercise, time data representing a point of time, and a value representing the level of exercise, and (v) a symbol representing one of an amount of change in a basal delivery rate, taking of medication, or illness, and time data representing a point of time. Indeed, it may be desirable to store other types of data. Also the "diary action card" screen comprises a spinner bar, this allowing the user to toggle between "edit", "delete", and "hide/show". Depending on the type of data, one or more of these actions may be allowable, e.g. some kind of data cannot be deleted or edited.

If the user selects "add" in the "diary-options" menu, the user is brought to a week view screen similar to the screen for the view option, e.g. comprising a spinner bar and a day selector feature. However, when a day and a type of data is selected from the spinner bar, pressing the ACCEPT key takes the user directly to an action card edit screen corresponding to the selected type of data to be entered, see FIG. 23 showing how a level and a time is entered for an exercise item to be added.

In the above aspects of a user interface for a drug delivery device has been described. Thus, in the following an illustrative drug delivery system suitable to be used in combination with a user interface incorporating one or more of the described aspects or features will be described. Although the present invention will be described with reference to the pump unit and the remote controller unit disclosed in FIGS. 24-29, it should be understood that the present disclosure is broadly applicable to any form of system comprising a pump unit in combination with a controller unit or other external unit, e.g. a PC or PDA. For example, aspects of the present invention may be used with programmable ambulatory insulin infusion pumps of the sort currently commercially available from a number of manufacturers, including without limitation and by way of example, Medtronic MiniMed under the trademark PARADIGM, Insulet Corporation under the trademark OmniPod, Smiths Medical under the trademark Deltec COZMO, and others, these pumps either being provided with a remote control or being adaptable to be used with one.

Figure 24:
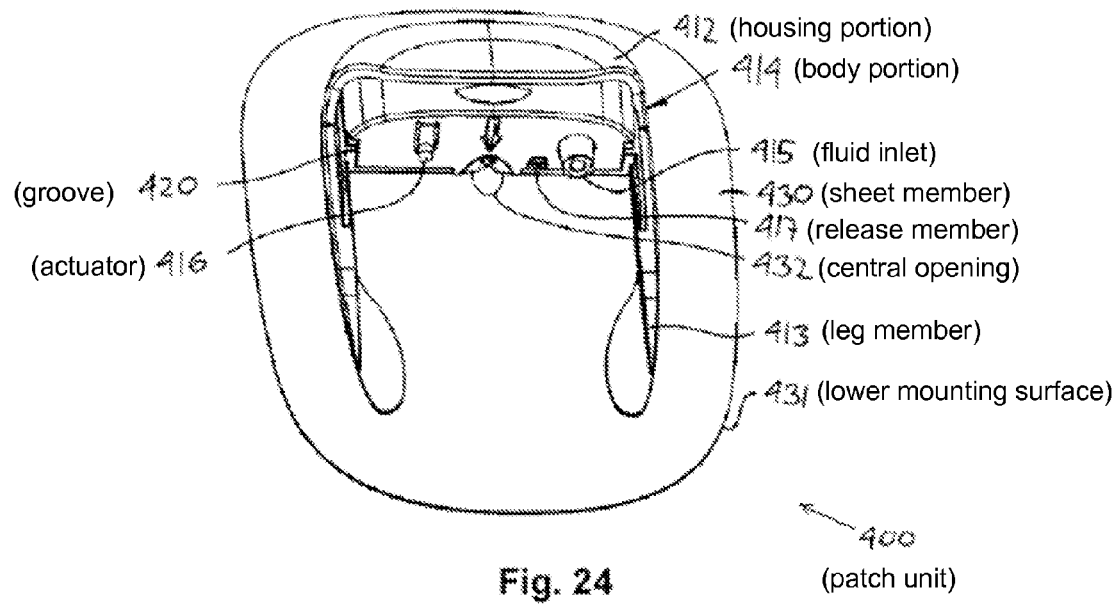
FIG. 24 shows the patch unit of FIG. 5 in greater detail.
Figure 25:
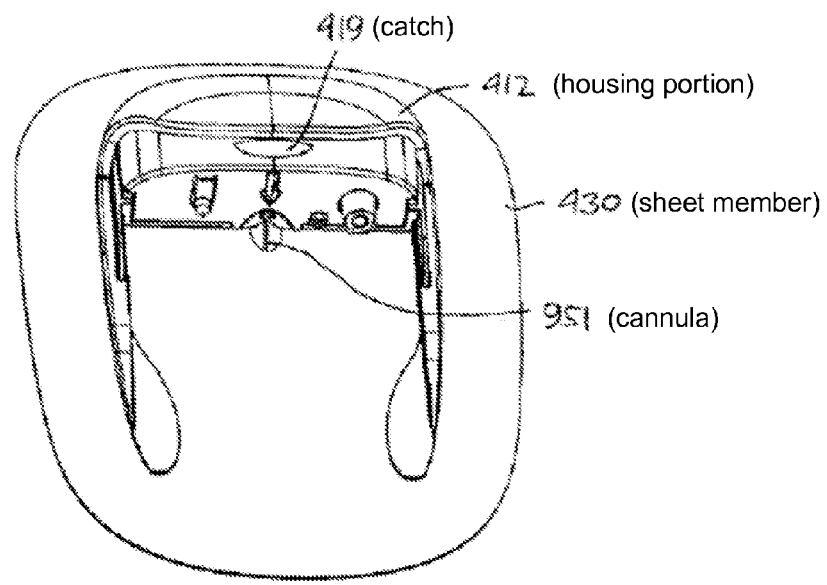
FIG. 25 shows the patch unit of FIG. 7 in an actuated state.

FIG. 24 shows a skin-mountable device in the form of a patch (or cannula) unit 400. The patch unit comprises a relatively rigid body portion 414 arranged on a flexible sheet member 430 with a lower mounting surface 431 provided with an adhesive allowing the sheet to be adhered to a skin surface of a subject. The sheet member comprises a central opening 432 through which a cannula can be inserted. The body portion comprises a housing portion 412 in which a cannula inserting mechanism is arranged, see below. The body portion further comprises two slider leg members 413 extending from the housing, the legs adding stiffness to the patch and further serves as guiding means when a pump/reservoir unit is attached the patch unit, see below. The housing is provided with a set of opposed grooves 420 serving as attachment means for a packaging and subsequently for a pump unit. The housing further comprises a fluid inlet 415 adapted to be mounted in fluid communication with a corresponding fluid outlet from an attached pump unit 450, an actuator 416 for actuating an electrical contact on the attached pump, and a release member 417 adapted to release a cannula inserting mechanism when the pump unit is attached for the first time, the cannula being inserted through the opening 432. The housing portion 412 also comprises a catch 419 adapted to engage a corresponding coupling structure on the pump unit. As appears, when the cannula 951 is inserted (see FIG. 25), it is protected by the pump unit, however, the pump unit can be removed for subsequent inspection of the insertion site as shown in FIG. 26.

Figure 26:
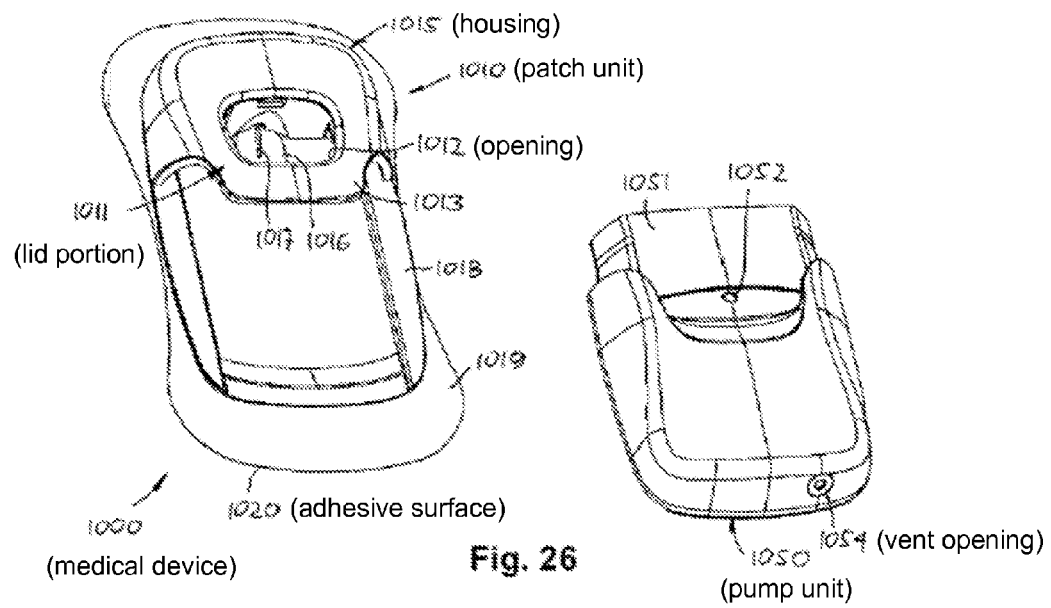
FIG. 26 shows a patch unit with a pump unit partly attached.
Figure 27:
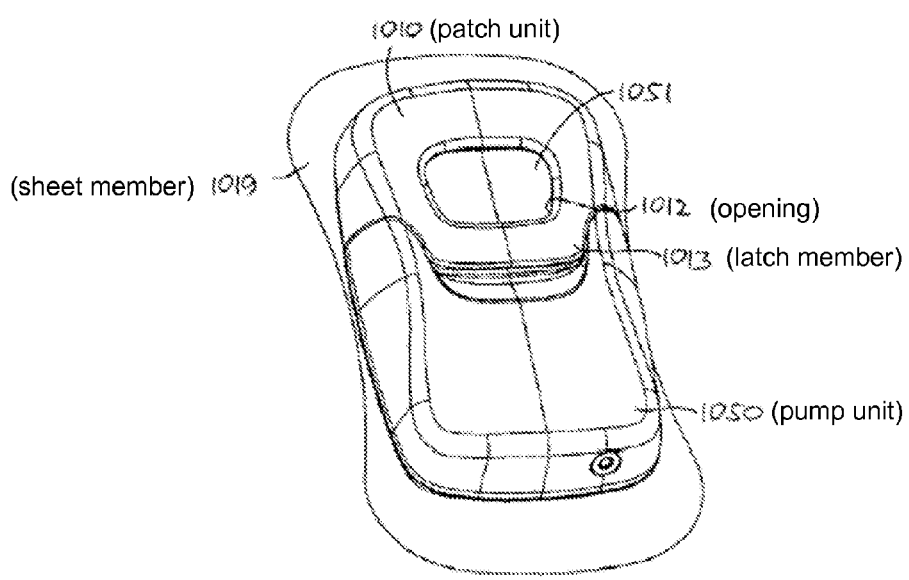
FIG. 27 shows the pump unit of FIG. 9 fully attached to the patch unit.

FIG. 26 shows an alternative embodiment of a patch unit 1010 with a pump unit 1050 by its side, and FIG. 27 shows the pump unit fully but releasably attached. More specifically, FIG. 26 shows an embodiment of a medical device 1000, comprising a cannula unit 1010 of the type shown in FIG. 24 and a thereto mountable pump (or reservoir) unit 1050. In the shown embodiment the cannula unit comprises a housing 1015 with a shaft into which a portion 1051 of the pump unit is inserted. The shaft has a lid portion 1011 with an opening 1012, the free end of the lid forming a flexible latch member 1013 with a lower protrusion (not shown) adapted to engage a corresponding depression 1052 in the pump unit, whereby a snap-action coupling is provided when the pump unit is inserted into the shaft of the cannula unit. Also a vent opening 1054 can be seen. The housing 1015 is provided with a pair of opposed legs 1018 and is mounted on top of a flexible sheet member 1019 with a lower adhesive surface 1020 serving as a mounting surface, the sheet member comprising an opening 1016 for the cannula 1017.

As appears, from the housing of the cannula unit extends a cannula at an inclined angle, the cannula being arranged in such a way that its insertion site through a skin surface can be inspected (in the figure the full cannula can be seen), e.g. just after insertion. In the shown embodiment the opening in the lid provides improved inspectability of the insertion site. When the pump unit is connected to the cannula unit it fully covers and protects the cannula and the insertion site from influences from the outside, e.g. water, dirt and mechanical forces (see FIG. 27), however, as the pump unit is detachable connected to the cannula unit, it can be released (by lifting the latch member) and withdrawn fully or partly from the cannula unit, this allowing the insertion site to be inspected at any desired point of time. By this arrangement a drug delivery device is provided which has a transcutaneous device, e.g. a soft cannula as shown, which is very well protected during normal use, however, which by fully or partly detachment of the pump unit can be inspected as desired. Indeed, a given device may be formed in such a way that the insertion site can also be inspected, at least to a certain degree, during attachment of the pump, e.g. by corresponding openings or transparent areas, however, the attached pump provides a high degree of protection during use irrespective of the insertion site being fully or partly occluded for inspection during attachment of the pump. In the shown embodiment an inclined cannula is used, however, in alternative embodiments a needle or cannula may be inserted perpendicularly relative to the mounting surface.

Figure 28:
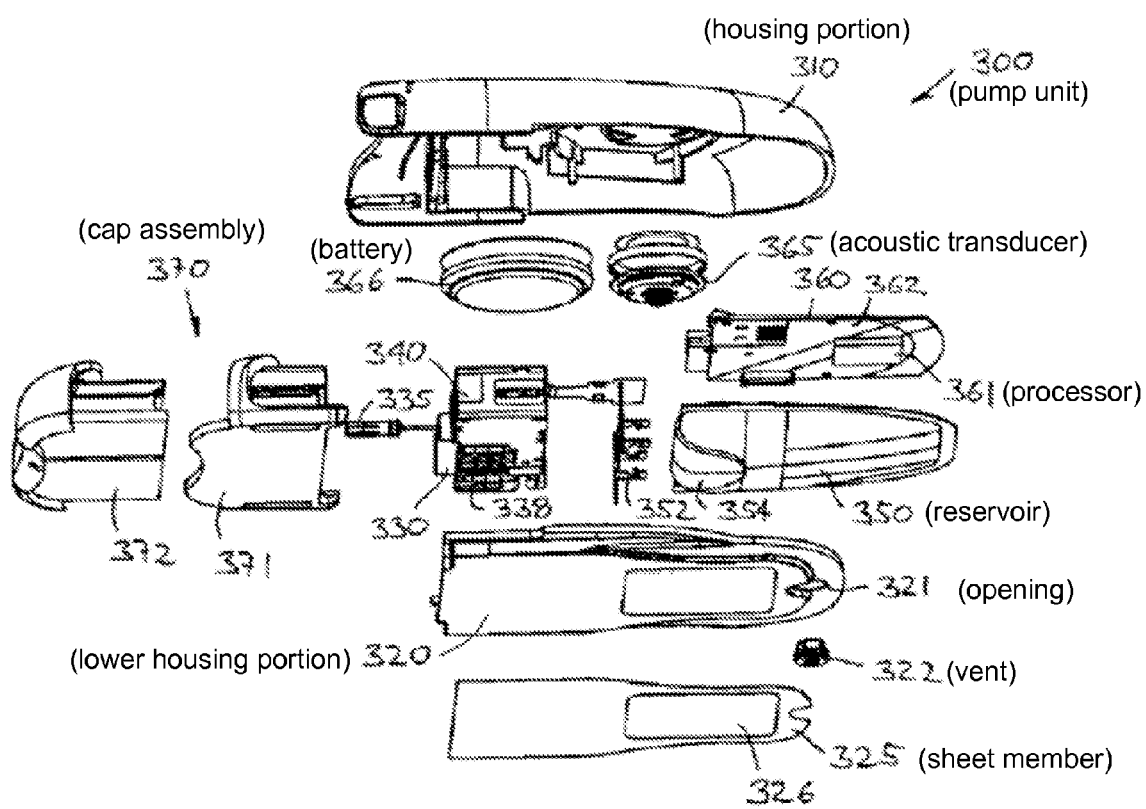
FIG. 28 shows in an exploded view a pump unit.

FIG. 28 shows in an exploded view a pump unit 300 of the same type as in FIG. 12. The pump unit comprises an upper housing portion 310 and a lower housing portion 320 which in an assembled state provides a water-protected enclosure for the additional components of the reservoir unit: A pump assembly 330, an actuator 340, a reservoir 350, and electronic control means 360. In an initial state as supplied to the user, a protective cap assembly 370 is attached to the unit.

The lower housing portion is made from a transparent material allowing a reservoir (see below) to be inspected by a user from the outside, and comprises an opening 321 in which a water repelling vent 322 is arranged. A sheet member 325 with a window opening 326 is attached to the lower surface of the lower housing portion, this masking the transparent portion except for a window over the reservoir. The sheet member may be used to display user information, e.g. type and amount of drug.

The pump assembly 330 is in the form of a membrane pump comprising a piston-actuated pump membrane with flow-controlled inlet- and outlet-valves. The pump has a general layered construction comprising a number of body members between which are interposed flexible membrane layers, whereby a pump chamber, inlet and outlet valves, and one or more safety valves can be formed, the layers being hold together with clamps 338. The pump further comprises a fluid connector 335 in the form of hollow connection needle slidably positioned within the pump (for illustrative purposes shown outside of the pump), this allowing the pump to be connected with reservoir when the protective cap assembly 370 is activated. For a more detailed description of such a membrane pump reference is made to applicants co-pending application WO 2006/089958, which is hereby incorporated by reference.

The pump actuator is in the form of a coil actuator to which the pump assembly is attached by a clamp. For a more detailed description of such a coil actuator reference is made to the description of FIGS. 1-9 above and applicants co-pending application WO 2005/094919, which is hereby incorporated by reference.

The drug reservoir is in the form of a flexible, pre-filled collapsible pouch 350 comprising a needle-penetratable septum 354 allowing the fluid connector to be pushed into the reservoir without leakage, thereby providing a fluid communication with the pump. A clip holder 352 is attached to the reservoir, this allowing the reservoir to be attached to the housing without influencing the reservoir per se. Under the reservoir (as seen from the lower surface of the unit) is arranged a sheet (not shown) comprising a contrast-enhancing pattern, e.g. a black line on a white background, allowing for easier visual identification of impurities in the drug, e.g. fibrillation in insulin.

The electronic control means 360 comprises a PCB or flex-print 362 with a processor 361 for controlling the pump assembly, a battery 366, an acoustic transducer 365 providing an alarm and communication interface with the user, as well as a contact mounted on the actuator allowing the control means to be activated by the user when taken into use for the first time (via the actuator 216). The control means may comprise a receiver and/or a transmitter allowing the reservoir to communicate wirelessly with a remote controller.

The protective cap assembly 370 comprises an attachment member 371 initially locked to the reservoir unit and an activation "push button" member 372 slidingly attached to the attachment member. When the reservoir unit is removed from its primary packaging (not shown) the user depresses the activation member towards the reservoir unit. This actuation results in three actions taking place: A first protrusion on the activation member will actuate a contact on the reservoir unit, this activating the electronics, and a second protrusion will engage the pump assembly and push the fluid connector 335 out from the pump assembly and into the reservoir, thereby establishing a fluid communication between the reservoir and the pump. Thirdly, depression of the activation member will "unlock" the attachment member and allow it, and thereby the activation member, to be removed from the reservoir unit. Thereafter the reservoir unit can be connected to the patch unit.

Figure 29:
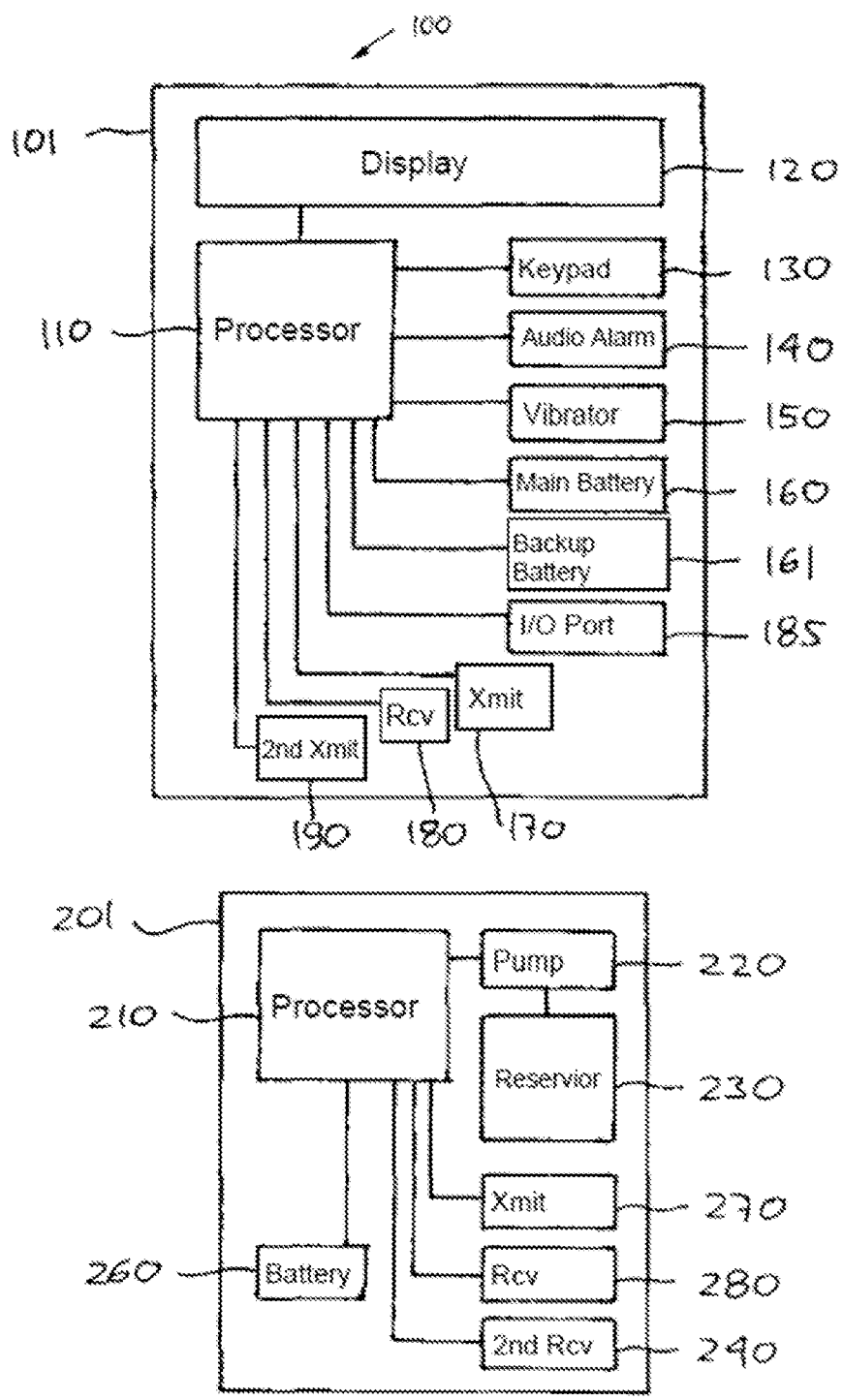
FIG. 29 shows a schematic representation of a process unit and a control unit.

FIG. 29 shows a schematic representation of a process unit 200 (here corresponding to the pump unit 1050 of FIG. 26) and a controller unit 100 (here in the form of a wireless "remote controller" or "external communication device" for the pump unit). It is considered that the general design of such units is well known to the skilled person, however, for a more detailed description of the circuitry necessary to provide the desired functionality of the present invention reference is made to US 2003/0065308 which is hereby incorporated by reference.

More specifically, FIG. 29 depicts a simplified block diagram of various functional components or modules (i.e. single components or groups of components) included in the pump unit 200 and remote controller 100. The remote controller unit includes a housing 101, a remote processor 110 including a CPU, memory elements for storing control programs and operation data and a clock, an LCD display 120 for providing operation for information to the user, a keypad 130 for taking input from the user, an audio alarm 140 for providing information to the user, a vibrator 150 for providing information to the user, a main battery 160 for supplying power to the controller, a backup battery 161 to provide memory maintenance for the controller, a remote radio frequency (RF) telemetry transmitter 170 for sending signals to the pump unit, a remote radio frequency (RF) telemetry receiver 180 for receiving signals from the pump unit, and a second transmitter 190. The controller further comprises a port 185, e.g. an infrared (IR) or RF input/output system, or a USB port for communicating with a further device, e.g. a blood glucose meter (BGM), a continuous blood glucose meter (CGM), a PC or a PDA.

As also depicted in FIG. 29, the pump unit 200 includes a housing 201, local processor electronics 210 including a CPU and memory elements for storing control programs and operation data, battery 260 for providing power to the system, a process unit RF telemetry transmitter 270 for sending communication signals to the remote unit, a process unit radio frequency (RF) telemetry receiver 280 for receiving signals from the remote unit, a second process unit receiver 240 (which may be in the form of a coil of an acoustic transducer used in an audio alarm for providing feedback to the user), a reservoir 230 for storing a drug, and a pump assembly 220 for expelling drug from the reservoir through a transcutaneous device to the body of a patient. In alternative embodiments the pump unit may also comprise an LCD display for providing information to the user, a keypad for taking input from the user, and a vibrator or other tactile actuator for providing information to the user. RF transmission may be in accordance with a standard protocol such as Bluetooth®. As appears, the system of FIG. 29 comprises first and second means of communication allowing a first and second group of data types to be transmitted between the two units. In this way different properties of the two means of communication can be used to secure that certain data, e.g. during pairing of the two devices using near-field communication, can be transmitted in a more controlled way whereas other data can be transmitted in a less controlled way using longer-distance communication.

In the above a number of features have been described for a user interface for a drug delivery system. The different features are part of a general information architecture for which a detailed disclosure can be found in applicants co-pending application WO 2007/000425.

In the above description of the preferred embodiments, the different structures and means providing the described functionality for the different components have been described to a degree to which the concept of the present invention will be apparent to the skilled reader. The detailed construction and specification for the different components are considered the object of a normal design procedure performed by the skilled person along the lines set out in the present specification.

The invention claimed is:

1. Device for displaying information, comprising:
   data storage circuitry for storing data,
   a display configured to display data to a user,
   a processor configured to control the display and the data storage circuitry, and
   user input circuitry,
   wherein the processor is configured to store data organized as data units, each data unit comprising:
      time data,
      type data, and
      information data,
   wherein the processor is configured to control the display to:
      graphically display an aggregate period view comprising at least two period views,
      graphically display a single period view,
      graphically display a data type symbol corresponding to a given data type,
      graphically display at least one data type symbol for every period view, and
      display a card view comprising information data corresponding to a selected data type symbol,
   wherein the user input circuitry allows the user to:
      select a desired period view from the aggregate period view, the display thereby displaying the selected period view,
      select a desired symbol from the selected period view, the display thereby displaying the card view showing at least a portion of the corresponding information data, and
      select a card view showing information data of the next or the previous data unit stored in the data storage circuitry, the order of the data units being defined by the corresponding time data for the data units.

2. The device as in claim 1, wherein the processor is configured to control the display to display a view menu allowing the user to select between two or more types of data type symbols, or combinations of data type symbols, to be displayed for a given aggregate period view or a period view.

3. The device as in claim 2, wherein the user input circuitry allows the user, for the selected type of data type symbol or combination of data type symbols, to select a card view showing information data of the next or the previous data unit stored in the data storage circuitry, the order of the data units being defined by the corresponding time data for the data units.

4. The device as in claim 1, wherein the aggregate period view represents a week and the period view represents a day.

5. The device as in claim 1, wherein the user input circuitry allows the user to select a first mode in which selected data can be displayed, and a second mode in which data can be entered using the user input circuitry, the entered data being stored in the data storage circuitry.

6. The device as in claim 5, wherein the processor is configured to control the display to display a data entry menu allowing the user to select between two or more types of data, the selected type of data allowing the user to enter information data corresponding to the selected type.

7. The device as in claim 6, wherein the user input circuitry allows the user to select a period from a displayed aggregate period view, the selected period at least partially determining the time data for the data to be entered.

8. The device as in claim 1, wherein a data unit comprises data from one of the following groups of data:
   type data representing a blood glucose value, time data representing a point of time, and information data representing the blood glucose value,
   type data representing a meal, time data representing a point of time, and information data representing a value representing a characteristic of the meal,
   type data representing a bolus delivery, time data representing a point of time, and information data representing a size of a bolus,
   type data representing exercise, time data representing a point of time, and information data representing a value representing the level of exercise, and
   type data representing one of a change in a basal delivery rate, taking of medication, or illness, and time data representing a point of time.

9. The device as in claim 8, wherein each type data is associated with a graphical data type symbol configured to be displayed on the display.

10. The device as in claim 1, wherein the user input circuitry comprises up-down, left-right and select controls, the up-down controls being configured to select between a plurality of diary item options to be displayed, the left-right and select controls being configured to select the desired period view from the aggregate period view and select the desired symbol from the selected period view.

* * * * *